United States Patent
Hess et al.

(10) Patent No.: US 10,054,518 B2
(45) Date of Patent: Aug. 21, 2018

(54) SECTIONING VOLUME SAMPLES

(71) Applicant: Howard Hughes Medical Institute, Chevy Chase, MD (US)

(72) Inventors: Harald F. Hess, Leesburg, VA (US); David Peale, San Diego, CA (US); Patrick R. Lee, San Diego, CA (US)

(73) Assignee: Howard Hughes Medical Institute, Chevy Chase, MD (US)

( * ) Notice: Subject to any disclaimer, the term of this patent is extended or adjusted under 35 U.S.C. 154(b) by 684 days.

(21) Appl. No.: 14/533,904

(22) Filed: Nov. 5, 2014

(65) Prior Publication Data

US 2015/0135917 A1 May 21, 2015

Related U.S. Application Data

(60) Provisional application No. 61/900,262, filed on Nov. 5, 2013.

(51) Int. Cl.
*B26D 1/00* (2006.01)
*G01N 1/06* (2006.01)

(52) U.S. Cl.
CPC ......... *G01N 1/06* (2013.01); *G01N 2001/065* (2013.01); *Y10T 83/0448* (2015.04); *Y10T 83/148* (2015.04); *Y10T 83/6577* (2015.04)

(58) Field of Classification Search
CPC G01N 1/06; G01N 2001/065; Y10T 83/0448; Y10T 83/148; Y10T 83/6577
USPC ....................................... 83/915.5
See application file for complete search history.

(56) References Cited

U.S. PATENT DOCUMENTS

| | | | |
|---|---|---|---|
| 3,832,923 A | * | 9/1974 | Lassmann ............... G01N 1/06 83/152 |
| 4,697,489 A | | 10/1987 | Kim |
| 5,181,443 A | | 1/1993 | Sitte et al. |
| 5,551,326 A | | 9/1996 | Goodman |
| 5,752,425 A | | 5/1998 | Asakura et al. |
| 5,906,148 A | | 5/1999 | Aihara et al. |

(Continued)

FOREIGN PATENT DOCUMENTS

| | | |
|---|---|---|
| DE | 2265184 A1 | 9/1976 |
| EP | 2503315 A2 | 9/2012 |

OTHER PUBLICATIONS

"The Transmission Electron Microscope—Preparation of Specimen," 2 pages, captured by wayback machine on Apr. 29, 2012 at https://web.archive.org/web/20120429233542/http://www.nobelprize.org/educational/physics/microscopes/tem/preparation.html.

(Continued)

*Primary Examiner* — Andrea Wellington
*Assistant Examiner* — Samuel A Davies
(74) *Attorney, Agent, or Firm* — DiBerardino McGovern IP Group LLC

(57) ABSTRACT

A microtome includes a blade located at an end of a trough that defines a cavity for holding a liquid; a sample block in which the at least one sample is suspended, the sample block is moveable relative to the blade such that when the sample block is passed across the blade a section is cut from the sample block; a plate that includes a support frame that defines an opening, and a transparent film extending across the opening, the transparent film being transparent to electrons, a grasper being configured to receive and retain the plate, wherein the grasper is moveable relative to the blade; and a pusher section that lacks the sample pusher section.

25 Claims, 33 Drawing Sheets

(56) References Cited

U.S. PATENT DOCUMENTS

| | | | |
|---|---|---|---|
| 6,041,686 | A | 3/2000 | Lihl et al. |
| 6,568,307 | B1 | 5/2003 | Gunther et al. |
| 7,430,946 | B2 | 10/2008 | Studer |
| 7,677,289 | B2 | 3/2010 | Hayworth et al. |
| 2003/0101858 | A1 | 6/2003 | Tamura et al. |
| 2006/0008790 | A1* | 1/2006 | Hayworth ............... G01N 1/06 435/1.1 |
| 2006/0266177 | A1 | 11/2006 | Studer |
| 2010/0175520 | A1 | 7/2010 | Kong et al. |
| 2012/0240737 | A1* | 9/2012 | Yang ...................... G01N 1/06 83/13 |

OTHER PUBLICATIONS

"ATLUM," Harvard Center for Brain Science, 2 pages, captured by wayback machine on May 23, 2013 at https://web.archive.org/web/20130523000126/http://cbs.fas.harvard.edu/sci ence/connectome-project/atlum.

"Microtome," from Wikipedia, the free encyclopedia, 11 pages, captured by wayback machine on Aug. 28, 2013 at https://web.archive.org/web/20130828083416/http://en.wikipedia.org/wiki/Microtome.

International Search Report and Written Opinion from counterpart International Patent Application No. PCT/US2014/064151, issued by Korean Intellectual Property Office as the International Searching Authority dated Feb. 16, 2015, 10 pages.

Kevin L. Briggman et al., "Volume electron microscopy for neuronal circuit reconstruction," Current Opinion in Neurobiology, vol. 22, No. 1, Feb. 1, 2012, pp. 154-161, XP055367777.

Extended European Search Report, counterpart European Patent Application No. 14859472.4, dated May 9, 2017, 11 pages.

\* cited by examiner

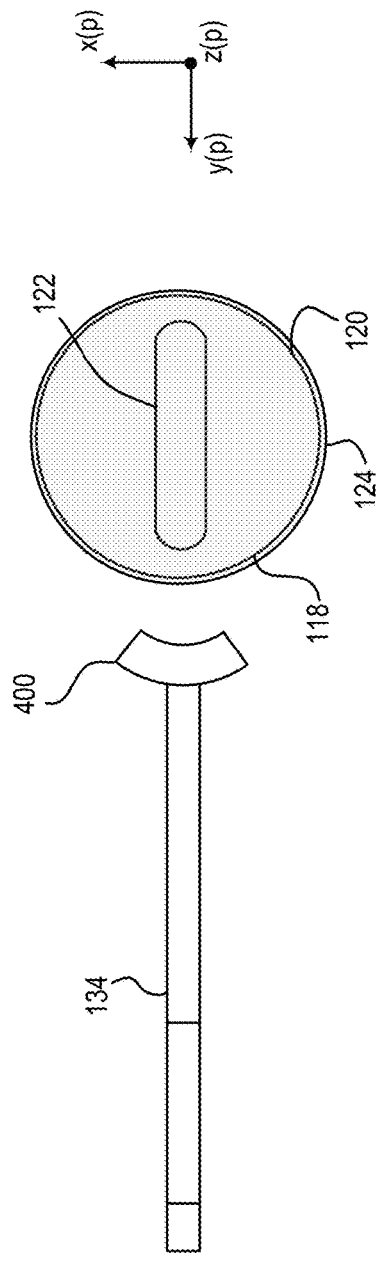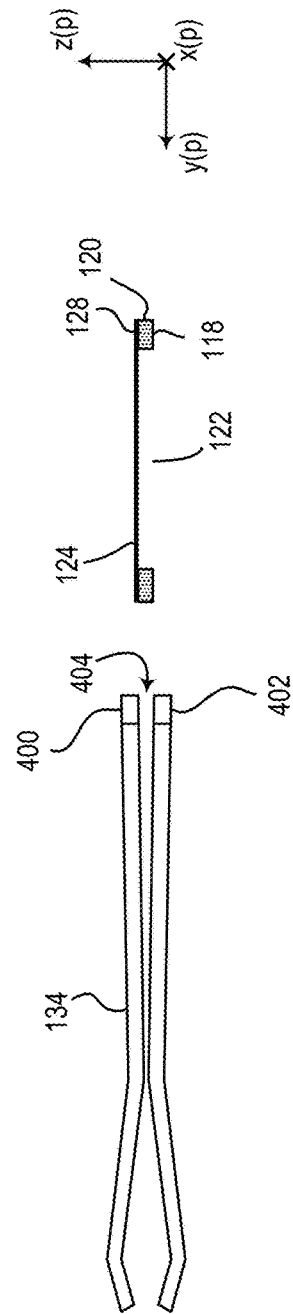

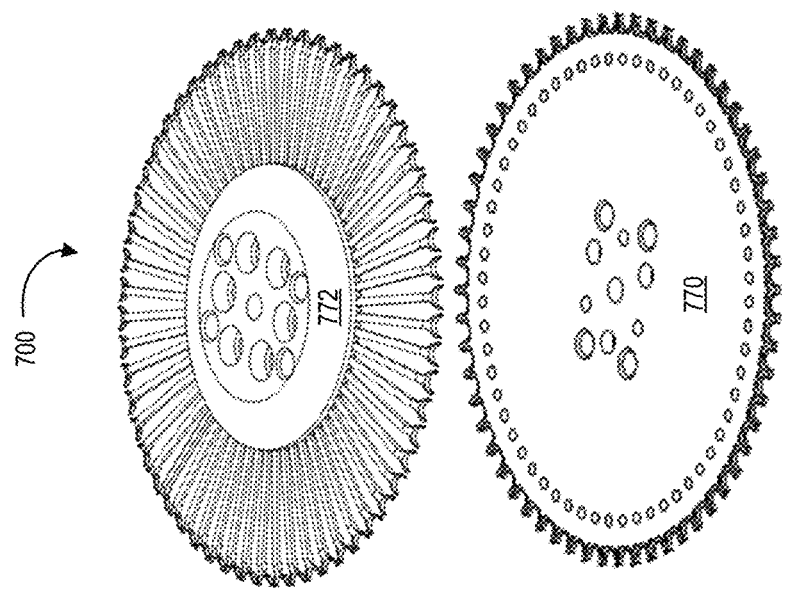
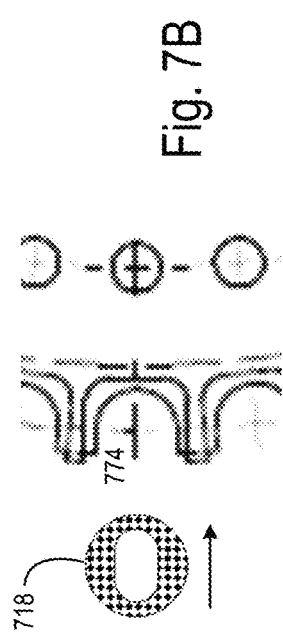
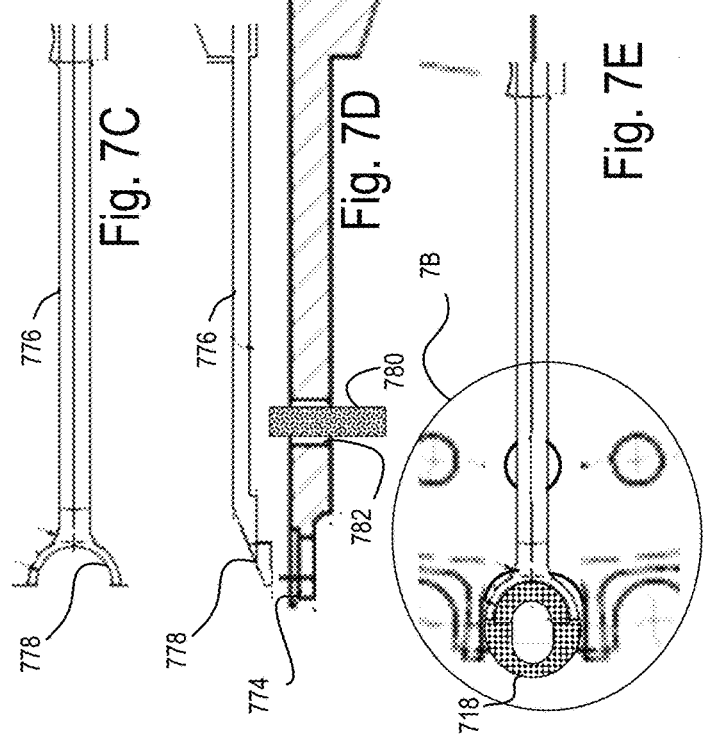
Fig. 7B
Fig. 7C
Fig. 7D
Fig. 7E
Fig. 7F

SECTIONING VOLUME SAMPLES

CROSS REFERENCE TO RELATED APPLICATION

This application claims the benefit of U.S. Provisional Application No. 61/900,262, filed Nov. 5, 2013, which is incorporated herein by reference in its entirety.

TECHNICAL FIELD

The disclosed subject matter relates to sectioning (cutting) of biological samples for use in a transmission electron microscope (TEM).

BACKGROUND

Preparation of a biological sample that is imaged in a TEM can be a complex procedure. Biological specimens (or samples) for use in a TEM are thin compared with specimens that are imaged using other types of microscopes such as optical microscopes. For a TEM, the specimen to be imaged should be of thin enough to allow electrons to travel through the specimen. The sample is prepared by cutting a very thin slice (section) from a sample embedded within a sample block, which can be made of plastic that infiltrates and surrounds the biological sample, polymerizes into a solid plastic block. The block is cut into thin sections by a blade using the microtome, which automates the process. Each section can be 20 nanometers (nm) to 2 micrometers (µm) thick.

Thin sectioning of samples suspended in sample blocks using an ultramicrotome is typically done by a highly skilled human operator. The level of skill, and the degree of effort to perform such sectioning without cutting errors can present challenges to sectioning volumes that are large enough to provide a complete understanding of the fine structure of organisms that are more complicated than small analids (worms).

SUMMARY

In some general aspects, a microtome cuts at least one sample suspended in a sample block of material. The microtome includes a blade located at an end of a trough that defines a cavity for holding a liquid; a sample block in which the at least one sample is suspended, the sample block is moveable relative to the blade such that when the sample block is passed across the blade a section is cut from the sample block; a plate that includes a support frame that defines an opening, and a transparent film extending across the opening; a grasper being configured to receive and retain the plate, wherein the grasper is moveable relative to the blade; and a pusher section that lacks the sample pusher section. The transparent film is transparent to electrons. The support frame extends along an x-y plane of the plate and includes a plane area that extends from the opening to an end along the x-y plane, and the support frame includes a thickness along the z axis of the plate that is perpendicular to the x-y plane of the plate, the thickness of the transparent film along the z axis of the plate being smaller than the thickness of the support frame. The plate is moveable relative to the blade.

Implementations can include one or more of the following features. For example, an extent of the pusher section can be as at least as long as the plane area along a direction that extends from one edge of the opening to another edge of the opening along the x-y plane.

The microtome can also include a blade actuation system to which the blade is physically coupled; a sample block actuation system to which the sample block is physically coupled; a plate actuation system to which the plate is physically coupled; a measurement system including at least one sensor positioned to sense at least one physical feature associated with one or more of the blade, the sample block, the plate, the trough, and the liquid; and a control system. The control system can be connected to: receive information from the measurement system, determine whether the at least one physical feature is within an acceptable range; and if it is determined that the at least one physical feature is outside the acceptable range, send one or more signals to the blade actuation system, the sample block actuation system, and the plate actuation system. The blade actuation system can be coupled to the trough; and the plate actuation system can be coupled to the grasper.

The pusher section can be a part of the sample block and the part is void of the sample. The pusher section of the sample block can be farther away from the blade than the sample suspended within the sample block when the sample block is positioned next to the blade before cutting. The pusher section can be a part of a blank block that is separate from the sample block and the blank block can be void of the sample. The microtome can include one or more additional pusher sections that lack the sample.

The grasper can include two pincers at an end, the two pincers defining a space therebetween. The space between the two pincers can have an adjustable extent that is adjustable to at least the thickness of the flat support frame.

In other implementations, a method of cutting at least one sample suspended in a sample block of material is described. The method includes passing the sample block across a blade one or more times; and with each passing of the sample block across the blade, cutting a section from the sample block, wherein one or more sections float on a liquid, and a last section of the one or more sections remains attached to the blade. The method includes positioning a plate that includes an imaging region in the liquid and under the one or more floating sections while the last section remains attached to the blade; clinging the one or more floating sections to the plate; and removing the last section that is attached to the blade from the blade after at least one section is clung to the plate.

Implementations can include one or more of the following features. For example, the blade can be located at the end of a trough that defines a cavity that holds the liquid. The method can include removing the plate from the cavity after the one or more floating sections are clung to the plate.

The plate can be positioned in the liquid and under the one or more floating sections by positioning the plate such that at least one sample of a section is positioned across the imaging region of the plate. The plate can be positioned in the liquid and under the one or more floating sections by moving one or more sections and the plate with respect to each other such that the sections ride up a meniscus of the liquid that initially separates sections from the plate.

The one or more floating sections can be clung to the plate by removing the liquid between the one or more floating sections and the plate. The one or more floating sections can be clung to the plate by lowering the one or more floating sections onto the plate such that the at least one sample of each floating section is positioned over the imaging region of the plate. The one or more floating sections can be clung to the plate by raising the level of the liquid before lowering the level of the liquid.

With each passing of the sample block across the blade after the first pass of the sample block across the blade, after the section is cut from the block, the section can stick to the last section that was cut and is floating in the liquid.

The method can include removing the plate from the liquid after the one or more floating sections are clung to the plate. The method can include removing liquid from the plate after the plate is removed from the liquid. The liquid can be removed from the plate after it is removed by blotting the liquid by touching the plate to an absorbent material.

The imaging region can be a transparent region. The transparent region of the plate can be a region that is transparent to electrons. The transparent region of the plate can include a plastic film across an opening defined within the plate, and the one or more floating sections can be clung to the plate by clinging at least a portion of each section that includes the sample to the plastic film.

The sample block can be passed across the blade by passing the sample block across the blade one time such that one section floats on the liquid, and the one section that floats on the liquid includes a sample region that includes the at least one sample and a pusher region that lacks the at least one sample. The floating section can be clung to the plate by lowering a level of the liquid so that the floating section is lowered onto the plate. The floating section can be clung to the plate by lowering the floating section onto the plate such that the sample region of the floating section is positioned over the imaging region of the plate and the pusher region is positioned over a non-imaging region of the plate.

At least one section cut from the sample block can include a sample region positioned adjacent to a pusher region that lacks the sample, and, the pusher region can be long enough to position the sample region over the imaging region of the plate before the at least one section is clung to the plate.

The sample region can be closer to the blade than the pusher region just before the sample block contacts the blade.

In other general aspects, a method of cutting at least one sample suspended in a sample block of material is described. The method includes passing the sample block across a blade one or more times; with each passing of the sample block across the blade, cutting a sample section from the sample block, wherein one or more sample sections float on a liquid; passing a blank block across the blade one or more times, wherein the blank block lacks the sample; and with each passing of the blank block across the blade, cutting a pusher section from the blank block, wherein one or more pusher sections float on the liquid and a last pusher section remains attached to the blade. The method includes positioning a plate that includes an imaging region in the liquid and under at least the one or more sample sections; clinging the one or more sample sections and the one or more pusher sections to the plate; and removing the last pusher section from the blade.

Implementations can include one or more of the following features. For example, blade can be located at an end of a trough that defines a cavity that holds the liquid. The method can include removing the plate from the cavity after the one or more sample sections and the one or more pusher sections are clung to the plate.

The plate can be positioned in the liquid and under the one or more sample sections by positioning the plate such that at least one of the samples of a sample section is positioned across the imaging region of the plate.

The one or more sample sections and the one or more pusher sections can be clung to the plate by removing the liquid between the one or more sample sections and the one or more pusher sections and the plate.

The one or more sample sections and the one or more pusher sections can be clung to the plate by lowering a level of the liquid relative to the plate so that all of the sections are lowered with the liquid onto the plate. The one or more sample sections can be clung to the plate by lowering the sample sections onto the plate such that the samples of the sample sections are positioned over the imaging region of the plate. The one or more sample sections and the one or more pusher sections can be clung to the plate by raising the level of the liquid before lowering the level of the liquid.

With each passing of the sample block across the blade after the first pass of the sample block, after the sample section is cut from the sample block, the sample section can stick to the last sample section that was cut and is floating in the liquid.

The plate can be positioned inside the liquid and under at least the one or more sample sections while the last pusher section remains attached to the blade. The last pusher section can be removed from the blade by removing the last pusher section from the blade after at least one of the sample sections is clung to the plate.

The imaging region can be a transparent region. The transparent region of the plate can be a region that is transparent to electrons. The plate can include a non-transparent region that provides a frame and defines the transparent region. The transparent region can include a plastic film that extends across the transparent region and is secured to the non-transparent region. The one or more sample sections and the one or more pusher sections can be clung to the plate by clinging at least a portion of each sample section to the plate so that the sample in each sample section is adjacent the transparent region, and clinging at least a portion of the one or more pusher sections to the plate so that the pusher sections extend across the non-transparent region.

The sample block can be passed across the blade by passing the sample block across the blade one time such that one sample section floats on the liquid. The blank block can be passed across the blade by passing the blank block across the blade one time such that one pusher section floats on the liquid. The sample block can be passed across the blade by passing the sample block across the blade a plurality of times such that a plurality of sample sections float on the liquid. The blank block can be passed across the blade by passing the blank block across the blade a plurality of times such that a plurality of pusher sections float on the liquid.

The plate can be positioned in the liquid and under the one or more floating sections by moving one or more sections and the plate with respect to each other such that the sections ride up a meniscus of the liquid that initially separates sections from the plate.

In other general aspects, a method of cutting a sample suspended in a sample block of material is described. The method includes repeatedly passing a sample block across a blade located at the end of a trough that defines a cavity that holds a liquid; with each passing of the sample block across the blade, cutting a sample section from the sample block, wherein a plurality of sample sections float onto the liquid held within the trough and remain adhered to each other, and at least one of the sample sections or a pusher section that is void of the sample remains attached to the blade; clinging all of the plurality of sample sections to a plate that includes a transparent region; removing the at least one of the sample sections or the pusher section that is attached to the blade from the blade; detecting a relative physical feature between one or more of the blade, the trough, the liquid, the plate, and the sample block; and controlling one or more of the passing, the cutting, the clinging, and the removing based on the detected relative physical feature.

Implementations can include one or more of the following features. For example, the relative physical feature between one or more of the blade, the trough, the liquid, the plate, and the sample block can be detected by detecting a distance between the blade and the sample block before the sample block is passed across the blade.

The relative physical feature between one or more of the blade, the trough, the liquid, the plate, and the sample block can be detected by detecting an angle between the blade and the sample block before the sample block is passed across the blade. The relative physical feature between one or more of the blade, the trough, the liquid, the plate, and the sample block can be detected by detecting a distance between the plate and the blade. The relative physical feature between one or more of the blade, the trough, the liquid, the plate, and the sample block can be detected by detecting an electrical feature between the plate and the liquid.

The method can include positioning the plate in the cavity of the trough so that the plate passes into the liquid and under the plurality of sample sections while the at least one of the sample sections or the pusher section remains attached to the blade.

The at least one of the sample sections or the pusher section that is attached to the blade can be removed from the blade by removing the at least one of the sample sections or the pusher section after one or more sample sections in the plurality are clung to the plate.

All of the plurality of sample sections can be clung to the plate by sequentially clinging the plurality of sample sections to the plate. All of the plurality of sample sections can be clung to the plate by positioning the samples of the plurality of sample sections across the transparent region of the plate.

DESCRIPTION OF DRAWINGS

FIG. 4A is a top plan view of the plate with graspers;

FIG. 4B is a side cross sectional view of the plate with graspers of FIG. 4A;

FIG. 7B is a top plan view of an area of the plate storage device of FIG. 7A receiving a plate;

FIG. 7C is a top plan view of a retaining clamp of an upper half of the plate storage device of FIG. 7A;

FIG. 7D is a side cross sectional view of the retaining clamp of the upper half of the plate storage device of FIG. 7A and a shelf of a lower half of the plate storage device of FIG. 7A;

FIG. 7E is a top plan view of an area of the plate storage device of FIG. 7A in which a plate is received between the shelf and the retaining clamp of the plate storage device;

FIG. 7F is a perspective view of the upper and lower halves of the plate storage device of FIG. 7A;

DETAILED DESCRIPTION

Figure 1:
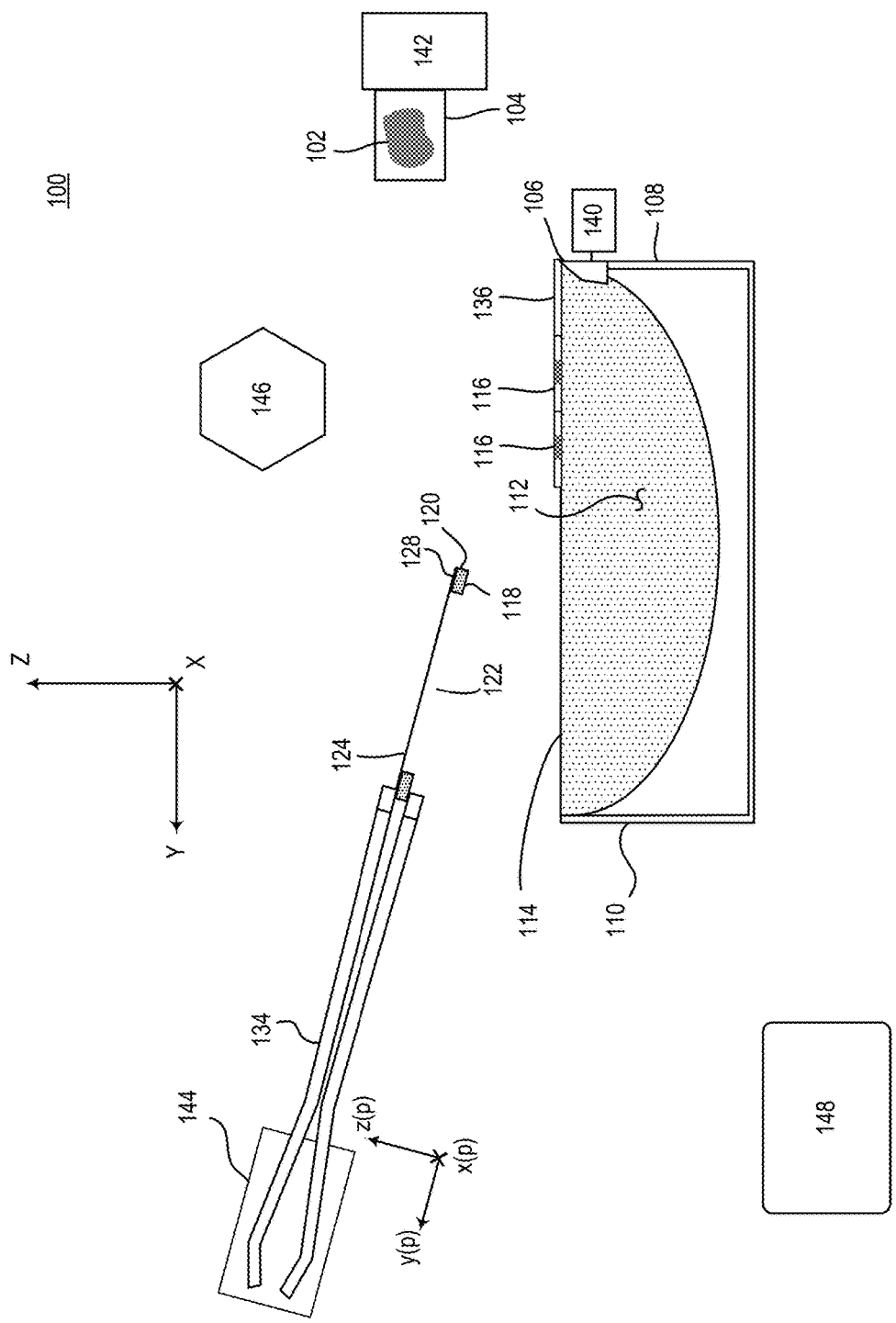
FIG. 1 is a block diagram of a microtome for cutting and placing transmission electron microscope (TEM) sections onto TEM plates.

Referring to FIG. 1, a microtome 100 is shown that automates the process of cutting and placing ultrathin transmission electron microscope (TEM) sections from sample blocks onto TEM plates (also called grids) are disclosed. The microtome implements a procedure that can operate twenty-four (24) hours a day, cutting and picking up high quality sections with a high degree of reliability. The technique disclosed herein can make it possible and feasible to completely section samples of volumes larger than those that have been previously accessible through human effort alone.

The microtome 100 cuts at least one biological sample 102 suspended in (for example, embedded in) a sample block 104 of material, such as plastic. In order to suspend or embed the sample 102 in the sample block 104, it can be placed in a mold and filled with a liquid substance such as paraffin (wax) or epoxy, which is later hardened to produce the sample block 104 that is readily cut.

The microtome 100 includes a blade 106 located at an end 108 of a trough 110 that defines a cavity 112 for holding a liquid 114. The blade 106 can be fixed to the end 108 of the trough 110 or it can be mounted to the end 108 of the trough 110 yet able to move relative to the trough 110. The blade 106 is a flat cutting edge of a block and its design can be based on the material and preparation of the sample to be imaged. The blade 106 can be shaped, for example, like a planar concave shape, a wedge shape, or a chisel shape (as shown in FIG. 1). The blade 106 can be made of a material such as glass or diamond. The section 116 (or sections 116 if a plurality are cut from the sample block 104) floats on the liquid 114 after being cut by the blade 106.

The sample block 104 is moveable relative to the blade 106 along any of the X, Y, and Z directions. When the sample block 104 is passed across the blade 104 (for example, along the Z direction as shown in FIGS. 13A-13D and 18A-18C), a section 116 is cut from the sample block 104, and after being cut, the section 116 floats on the liquid 114.

Figure 2A:
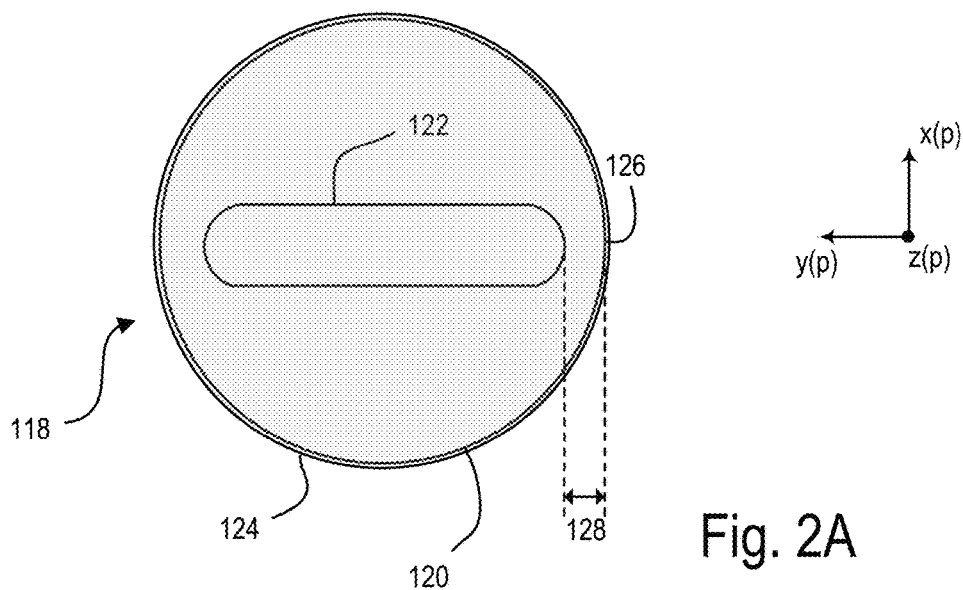
FIG. 2A is a top plan view of a plate for holding the cut sections.
Figure 2B:
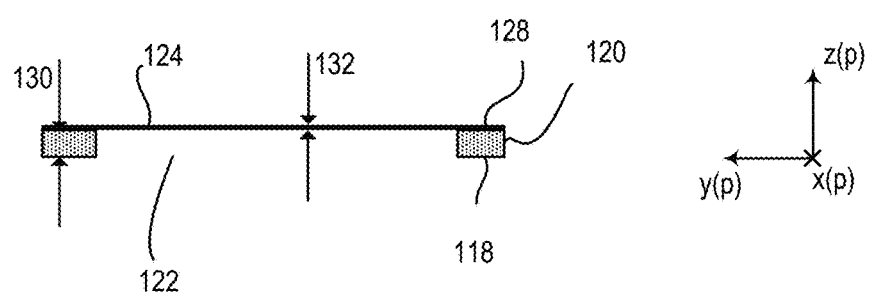
FIG. 2B is a side cross sectional view of the plate of FIG. 2A.

The microtome 100 includes a plate 118 that is moveable relative to the blade 106. Referring also to FIGS. 2A and 2B (which show larger views of the plate 118), the plate 118 includes a flat support frame 120 that defines an opening 122 and a transparent region 124. The transparent region 124 can be a transparent film that extends across the opening 122. In the example shown, the transparent film extends across the entire surface of the plate 118 to the edge of the flat support frame 120. It is possible that the transparent film can extend only partly across the surface of the flat support frame 120, as long as it covers the opening 122.

The flat support frame 120 extends along an x(p)-y(p) plane in the frame of the plate 118, and includes a frame length 128 that extends from the edge of the opening 122 to an end 126 of the flat support frame 120 along the x(p)-y(p) plate plane. The flat support frame 120 has a thickness 130 that extends along the z(p) axis of the plate 118, the z(p) axis of the plate 118 being perpendicular to the x(p)-y(p) plane of the plate 118. The thickness 132 of the transparent film 124 along the z(p) axis of the plate is smaller than the thickness 130 of the flat support frame 120. The flat support frame 120 of the plate 118 can be made from a suitably rigid material such as a metal (for example, copper, nickel, or alloys or copper and nickel), or etched silicon.

Figure 3:
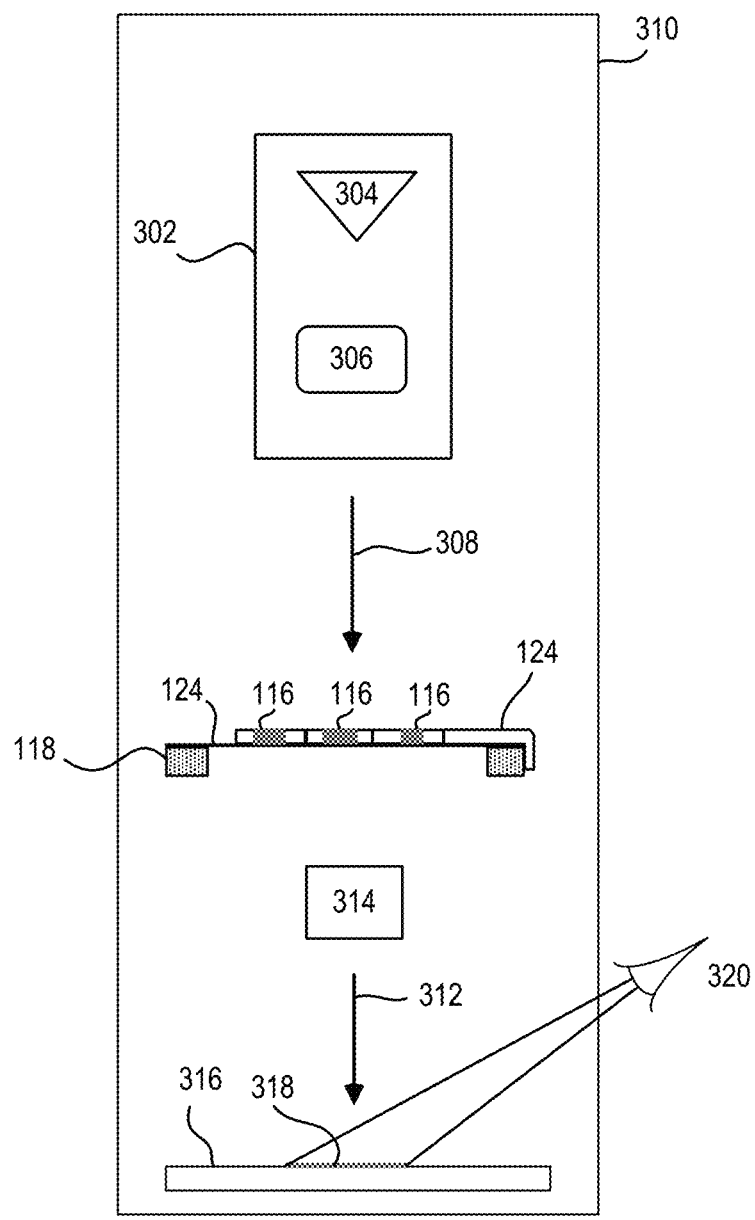
FIG. 3 is block diagram of an exemplary TEM that receives the plate with the cut sections.

Referring to FIG. 3, the transparent film 124 is transparent to electrons so that the section 116 (or sections if a plurality of sections 116 are cut) that will be clung to the plate 118 (and specifically, to the film 124) can be imaged with electrons in a transmission electron microscope (TEM) 300. The TEM 300 includes an electron source system 302 that includes an electron source 304 that produces a stream of electrons (or an electron beam 308), and electromagnetic beam optics 306 (such as electromagnetic lenses) that direct the electron beam 308 to the section 116. The components of the TEM 300 are within a chamber 310 that is held at a pressure approaching a vacuum environment. The electron beam 308 travels through the section 116; depending on the density of the sample suspended in the section 116, some of the electrons in the beam 308 are scattered along directions not in the path of the imaging or disappear from the beam. The unscattered and small-angle scattered electrons pass through the sample suspended in the section 116 as an electron beam 312. The electron beam 312 is focused with electromagnetic beam optics 314 onto a screen 316. The screen 316 produces a shadow image 318 of the sample with the different parts of the sample displayed in varied darkness according to its density. The image can be studied directly by an operator 320 or photographed with a camera for later observation.

Alternatively for scanning transmission electron microscopy, the electron beam 308 can be focused to a spot on the sample in the section 116 and scanned in a raster pattern across the sample in the section 116. The unscattered electron beam 312 or the small angle scattered electrons can be detected separately to form a raster image of the sample in the section 116.

Referring again to FIG. 1, the microtome 100 includes a grasper 134 that is moveable relative to the blade 106. As shown also in FIGS. 4A and 4B, the grasper 134 includes two opposing pincers 400, 402 at one end that receive and clamp down on the plate 118. The two pincers 400, 402 define a space 404 therebetween. The grasper 134 is configured to receive the plate 118 in the space 404 and to hold or clamp the plate 118 between the two pincers 400, 402. The space 404 between the two pincers 400, 402 has an extent that is adjustable to less than or equal to the thickness 130 of the flat support frame 120.

Figure 5A:
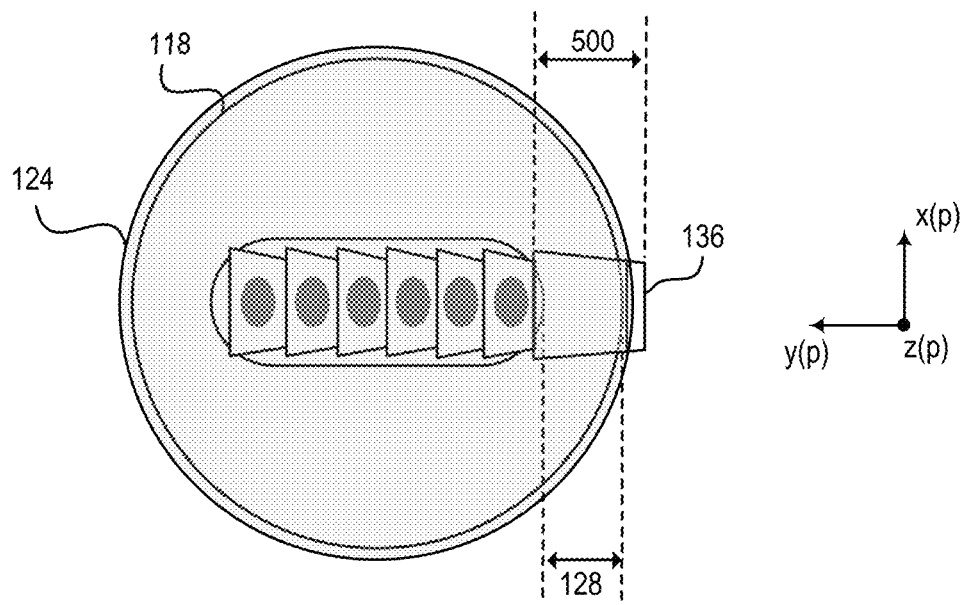
FIG. 5A is a top plan view of the plate in which cut sections have been attached.
Figure 5B:
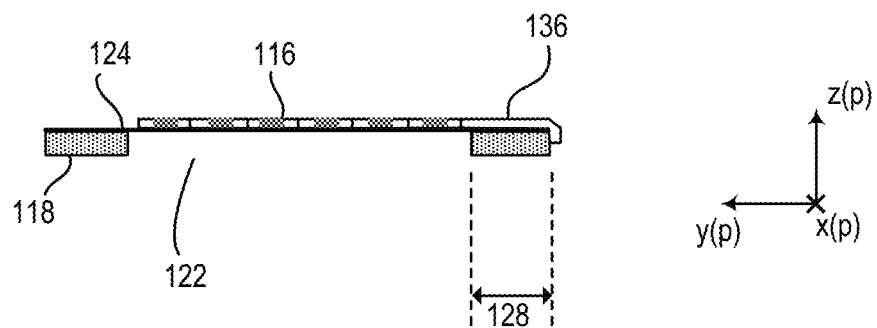
FIG. 5B is a side cross sectional view of the plate with the cut sections of FIG. 5B.

Referring again to FIG. 1, microtome 100 also includes a pusher section 136 that will be placed onto the flat support frame 120. The pusher section 136 is used to push the sections 116 over the transparent region 124 so that the samples of interest can be imaged. In some implementations, the pusher section 136 can include part of the sample that is not supposed to be visualized in transmission in a TEM. In other implementations, the pusher section 136 is void of a sample (that is, it lacks a sample). Referring also to FIGS. 5A and 5B, an extent 500 of the pusher section 136 is as at least as long as the frame length 128 along the x(p)-y(p) plane of the plate 118 along the y(p) direction of the plate 118. More details about the pusher section 136 are provided below.

Figure 7A:
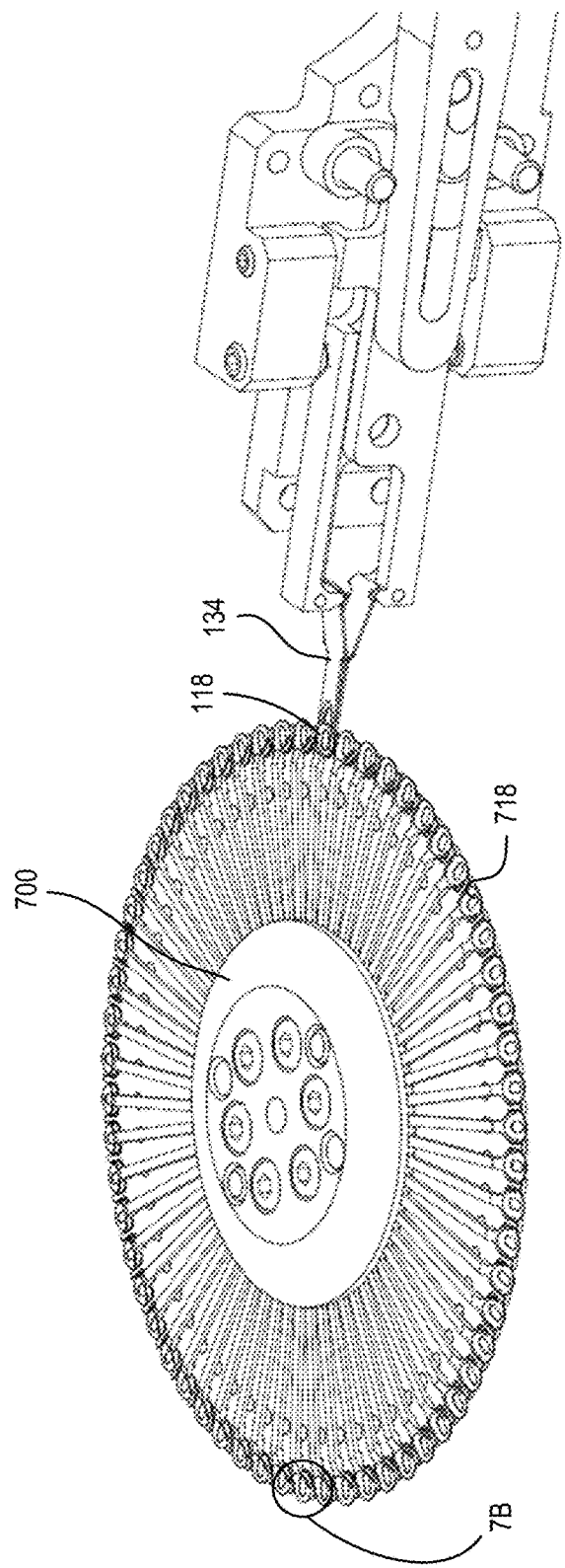
FIG. 7A is a perspective view of the grasper with the plate and a plate storage device for holding a plurality of plates.

Referring to FIGS. 7A-7C, the microtome 100 includes a storage device 700 for storing a plurality of plates 118. The storage device 700 can be used to store plates 118 that are blank (that lack any sections) or plates 118 to which one or more sample sections and pusher sections have been attached.

Each plate 118 can be clasped or gripped between two halves 770, 772 of a flat circular structure of the storage device 700: the bottom half 770 can have a plurality of shelves or pockets 774 where the plate 718 can be placed. To retain each plate 718, a spring arm 776 made of spring steel with a retaining clamp such as a "C" retainer 778 at the end is part of the top half 772 such that each of its C retainers 778 matches with the plate shelves. In a side view, the spring arm 776 can be lifted by a pin 780 that goes thru a hole 782 in the bottom half 770. Once the plate 718 is in between the shelf 774 and retaining clamp 778, the pin 780 is lowered, and the spring force of the spring arm 776 on to the plate 718 and the shelf 774 retains the plate 718 securely, as shown in 7B. Such a multiplate holder or storage device 700 can be used for automated storage and for both new plates 118 before sections are placed on them and also to receive plates 118 with sections after the sections have been placed on them. In addition, such a storage device 700 can easily be placed into a scanning transmission electron microscope chamber (such as the one shown in FIG. 3) to allow automated viewing of a plurality of sections on a plurality of plates 118 without reloading each plate 118. Finally, the thin geometry of such a multiplate holder allows the sections to be inclined with respect to the electron beam at large angles (for example, greater than 45 degrees) enabling imaging at multiple angles for electron tomography.

Referring again to FIG. 1, the microtome 100 also includes a set of actuation systems 140, 142, 144, each actuation system being connected to or coupled to its respective component of the microtome, a measurement system 146, and a control system 148. The physical coupling can be due to a direct physical connection between the actuation system and its respective component, or due to an indirect physical connection between the actuation system and its respective component.

Specifically, the microtome 100 includes an actuation system 140 physically coupled to the blade 106 so that movement imparted by the actuation system 140 (under control of the control system 148) is thereby imparted to the blade 106. The actuation system 140 can be directly physically coupled to the blade 106. Or, in some implementations such as when the blade 106 is fixed to the trough 110, the actuation system 140 can be physically connected to or coupled to the trough 110. In this way, the movement is imparted to the trough 110, and because the blade 106 is fixed to the trough 110, the motion of the blade 106 is also controlled.

Figure 6:
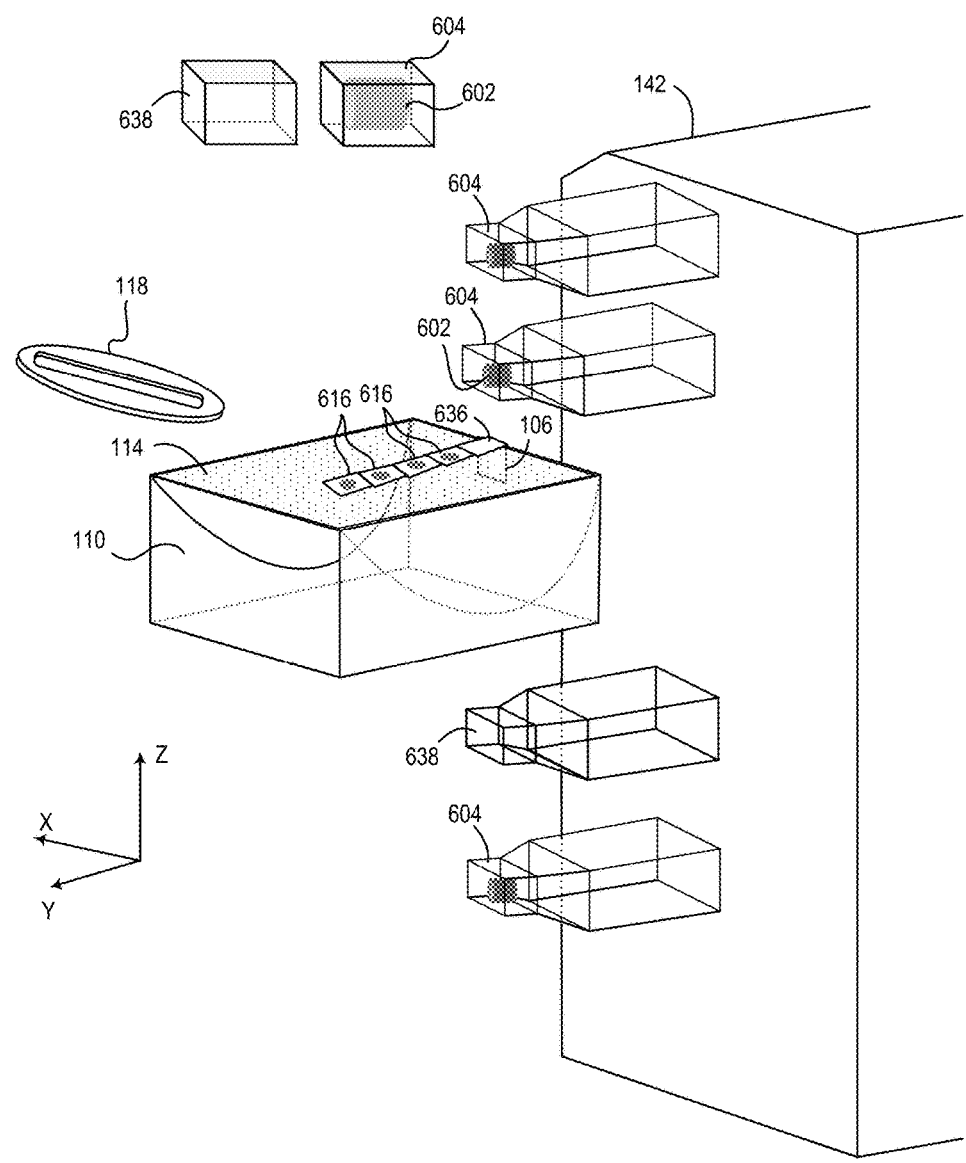
FIG. 6 is a perspective view of an exemplary trough holding liquid on which cut sections float, the plate, and one or more sample blocks and blank blocks of the microtome of FIG. 1.

The microtome 100 includes an actuation system 142 physically coupled to the sample block 104 so that movement imparted by the actuation system 142 (under control of the control system 148) is thereby imparted to the sample block 104. If a plurality of sample blocks 104 are used in the microtome 100 (such as shown in FIG. 6), then the actuation system 142 can be set up to control all of the sample blocks 104 simultaneously or sequentially.

The microtome 100 includes an actuation system 144 physically coupled to the plate 118 so that movement imparted by the actuation system 144 (under control of the control system 148) is thereby imparted to the plate 118. In some implementations such as when the plate 118 is held by the grasper 134, the actuation system 144 can be physically connected to or coupled to the grasper 134. In this way, the movement is imparted to the grasper 134, and because the plate 118 is held by the grasper 134, the motion of the plate 118 is also controlled.

The measurement system 146 includes one or more sensors that are positioned to sense at least one physical feature associated with one or more of the blade 106, the sample block 104, the plate 118, the trough 110, and the liquid 114. For example, the measurement system 146 can include one or more optical interferometers that measure a distance between the blade 106 and the sample block 104, and serve as a position sensing element of a feedback loop in conjunction with the control system 148, as discussed below with respect to FIGS. 23-25.

As another example, the measurement system 146 can include a machine vision apparatus that determines a relative position between the plate 118 and other parts of the microtome 100 such as the blade 106, the grasper 134, and a storage device (such as the storage device 700 shown in FIGS. 7A and 7B, which has securable openings for hundreds of plates 118) for the plate 118 or plates. Because the grasper 134 is controlled by an automated actuation system 144, and the tolerances of the mechanical parts within the microtome 100 are small, the machine vision system can enable reliable handling of the plate 118 as it is retrieved from the storage device that holds it before and after processing in the microtome 100.

As another example, the measurement system 146 can include an electrical or tactile detection system that detects when the plate 118 contacts the liquid 114. For example, such a detection system can sense an electrical continuity between the plate 118 and the liquid 114 or between the plate 118 and the storage device that holds it before and after processing in the microtome 100.

Figure 8:
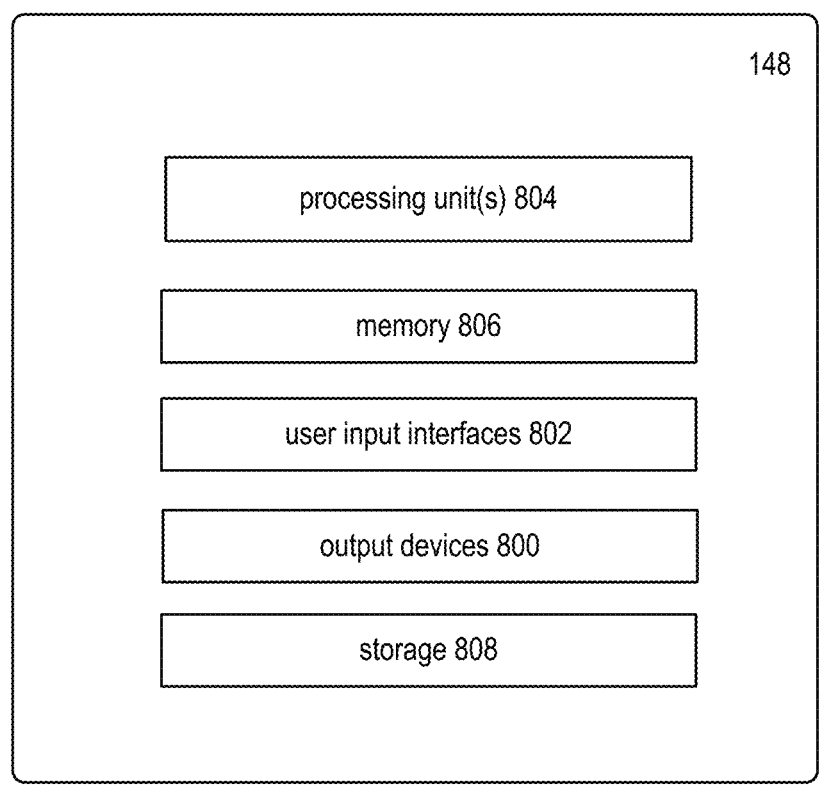
FIG. 8 is block diagram of an exemplary control system of the microtome of FIG. 1.

The control system 148 is connected to the measurement system 146, and to the each actuation system (such as systems 140, 142, 144) of the set. Referring to FIG. 8, the control system 148 can include a computer such as a workstation that has the ability to store, retrieve, and process data. Thus, the computer includes hardware such as one or more output devices 800 such as a monitor or a printer; one or more user input interfaces 802 such as a keyboard, a mouse, a touch display, or a microphone; one or more processing units 804, including specialized workstations for performing specific tasks; memory (such as, for example, random-access memory or read-only memory or virtual memory) 806; and one or more storage devices 808 such as hard disk drives, solid state drives, or optical disks. The processing units 804 can be stand-alone processors, or can be sub-computers such as workstations in their own right.

Figure 9:
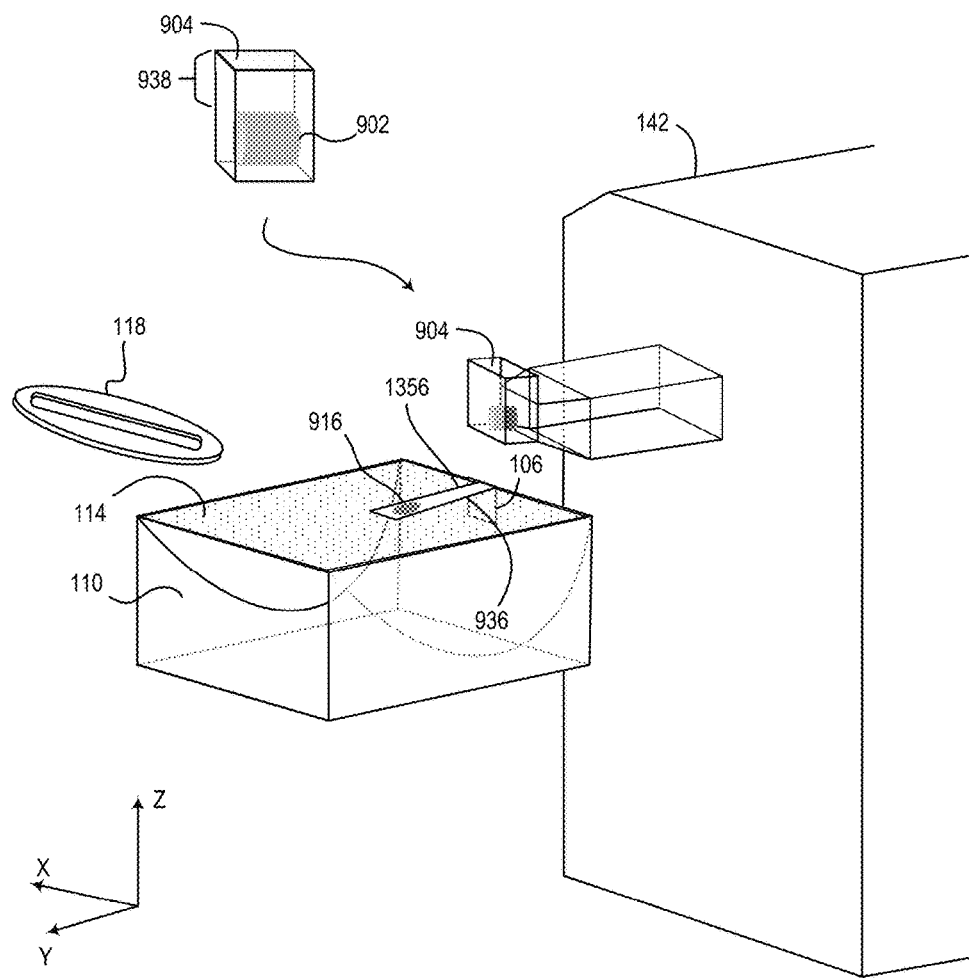
FIG. 9 is a perspective view of an exemplary trough holding liquid on which cut sections float, the plate, and one or more sample blocks of the microtome of FIG. 1.

In some implementations, such as shown in FIG. 9, the pusher section 936 is a part or region 938 of a sample block 904, and the part 938 is void of the sample to be visualized in the TEM 300 (even though the sample 902 is present in another part or region of the sample block 904 or the part 938 could include a sample that is not going to be visualized in the TEM 300). The pusher section 936 is cut from the sample block 904. The pusher section 936, when it is still within the sample block 904 (and before being cut as shown in FIG. 9), is farther away from the blade 106 than the sample 902 suspended within the sample block 904 when the sample block 904 is positioned next to the blade 106.

Figure 10:
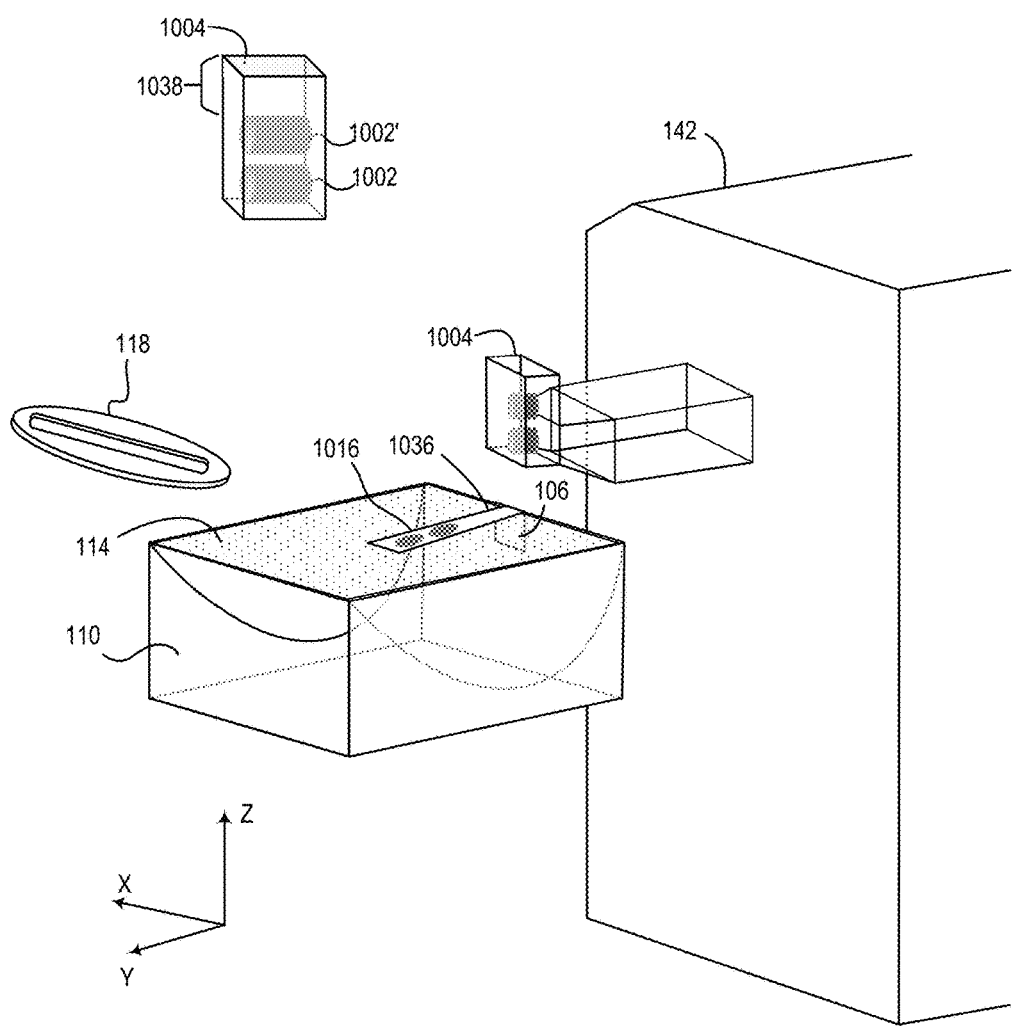
FIG. 10 is a perspective view of an exemplary trough holding liquid on which cut sections float, the plate, and one or more sample blocks of the microtome of FIG. 1.

Referring to FIG. 10, in other implementations, it is possible to suspend more than one sample 1002, 1002' in the sample block 1004. For example, two samples 1002, 1002' are suspended in the sample block 1004.

Referring to FIG. 6, in other implementations, the pusher section 636 is a slice taken from a blank block 638 that is separate from the sample block 604, the blank block 638 being entirely void of the sample 602 to be visualized in the TEM (though the blank block 638 could include a sample that is not going to be visualized in the TEM 300).

Figure 11:
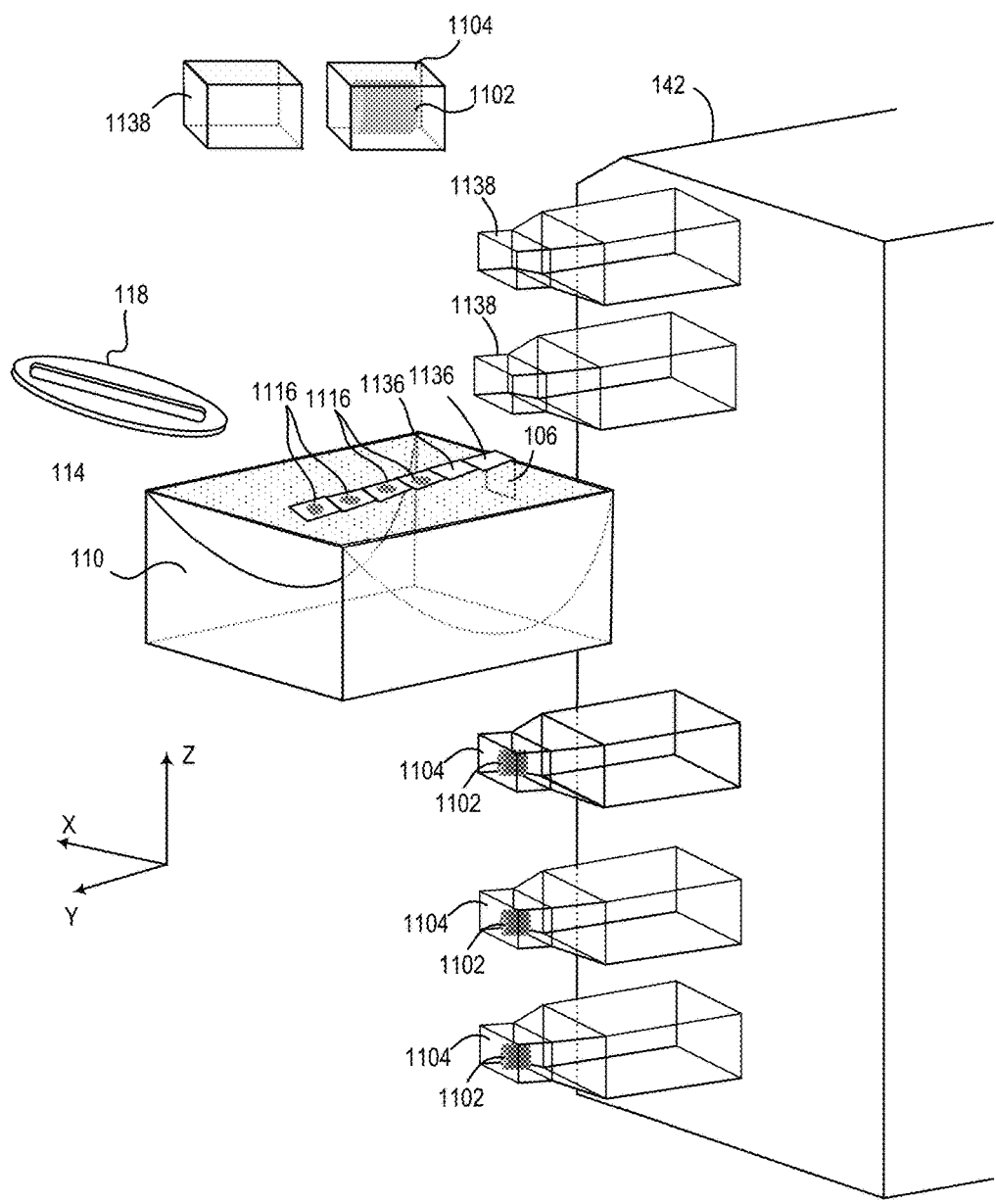
FIG. 11 is a perspective view of an exemplary trough holding liquid on which cut sections float, the plate, one or more sample blocks, and one or more blank blocks of the microtome of FIG. 1.

In other implementations, as shown in FIG. 11, the microtome 100 can include one or more additional pusher sections 1136 that lack the sample to be visualized in the TEM 300 and are taken from one or more blank blocks 1138.

Figure 12:
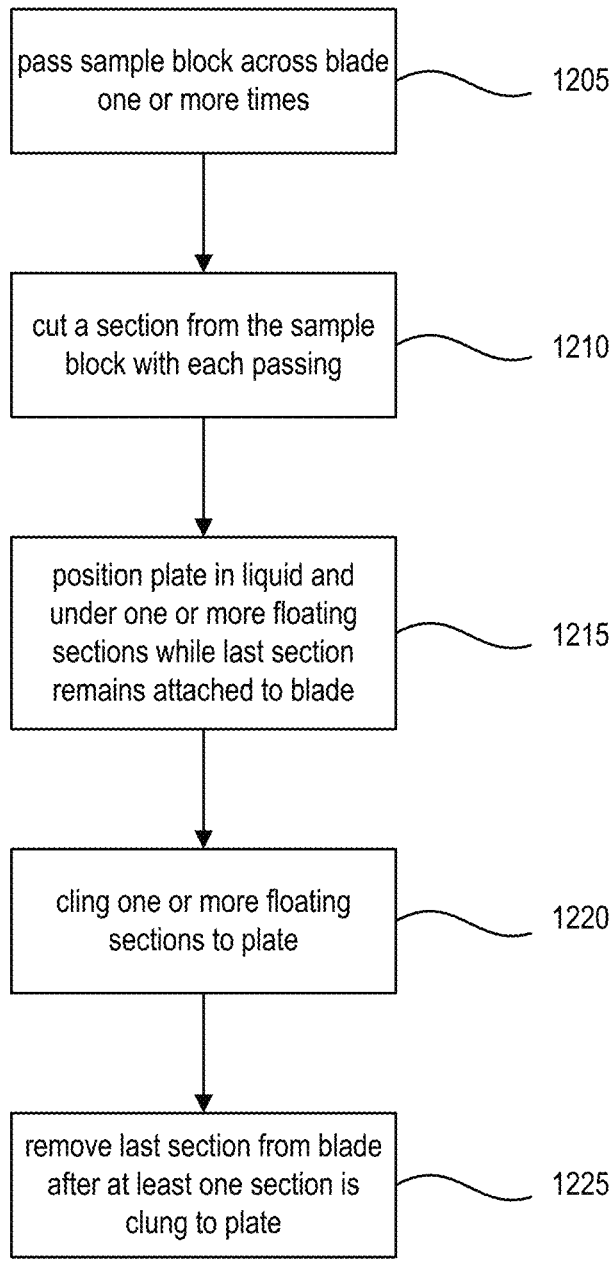
FIG. 12 is a flow chart of an exemplary procedure performed by the microtome of FIG. 1.

Referring to FIG. 12, a procedure 1200 is performed for cutting at least one sample (such as sample 902 of FIG. 9 or samples 1002, 1002' of FIG. 10) suspended in a sample block of material (such as block 904 of FIG. 9 or block 1004 of FIG. 10). The procedure 1200 is performed under control of the control system 148, which accesses information from the measurement system 146, performs an analysis on the information, and based on the analysis, determines how to adjust the components of the microtome 100 to cut the sample into sections. The control system 148 sends signals to one or more of the actuations systems 140, 142, 144 to control the movement of the blade 106, the sample block 904, 1004, and the plate 118.

When describing the procedure 1200, reference is made to FIGS. 9, 13A-13D, 14A-14B, 15A-15F, and 16A-16D, which describe the sample block 904 that includes only one sample 902. The procedure 1200 is also applicable to a sample block having a plurality of samples, such as the sample block 1004, which includes two samples 1002, 1002'. The sample block 904 is passed across the blade 106 one or more times (1205). In FIGS. 13A-13D, the progression of the sample block 904 is shown as it is passed across the blade 106 one time along the −Z direction of the microtome 100. With each passing of the sample block 904 across the blade 106, a section 916 is cut from the sample block 904 (1210). The one or more sections 916 float on the liquid 114, and the last section 1356 of the one or more sections 916 remains attached to the blade 106. In FIGS. 9 and 13A-13D, the sample block 904 is passed once across the blade 106. Moreover, FIG. 9 shows the microtome 100 at a time after step 1210 is completed; thus, the last section 1356 is still attached and the last section 1356 is the only section that was cut before the next steps, which involve the plate 118. Additionally, in FIG. 9, the next step in the procedure 1200 is not yet completed or performed.

Because the procedure involves very thin sections being formed, it is possible that not every passing of the sample block by the blade 106 results in a successful section being cut (a successful section may be one that is not ripped or wrinkled). If, for some reason, a section is not properly or successfully cut, the control system 148 can be set up to detect such an unsuccessful cut (by receiving a signal from the measurement system and/or vision systems 146) and the control system 148 could send instructions to the one or more actuation systems to make a second, or a further pass or passes until the desired cut is achieved.

Figure 15A:
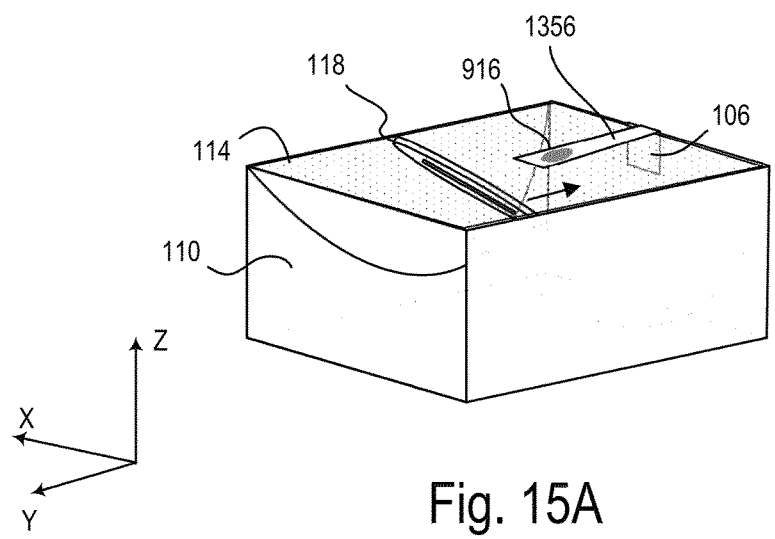
Figure 15B:
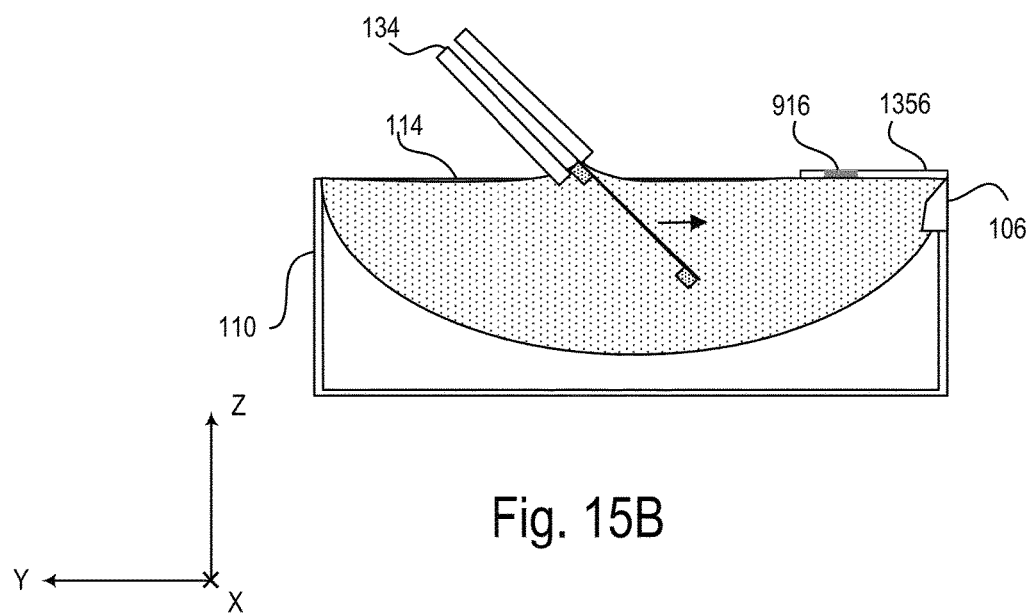
Figure 15C:
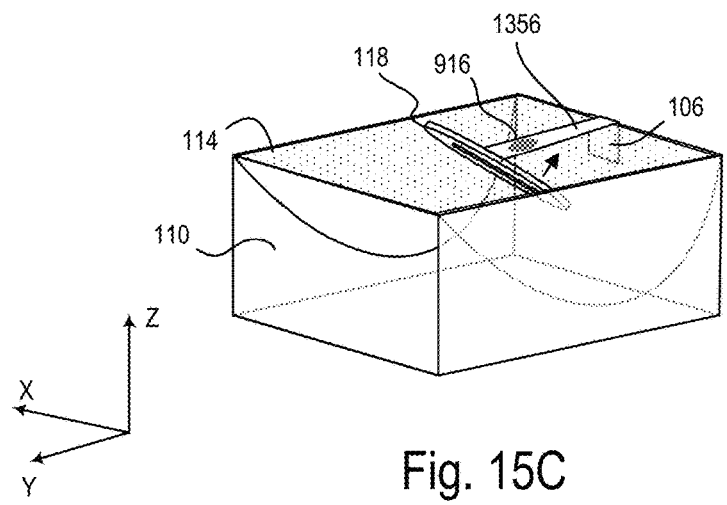
Figure 15D:
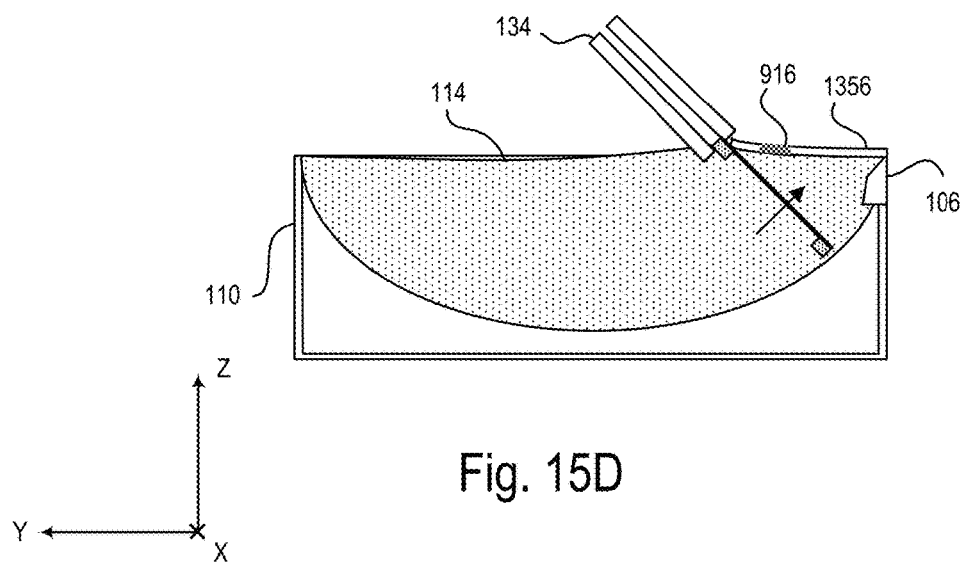
Figure 15E:
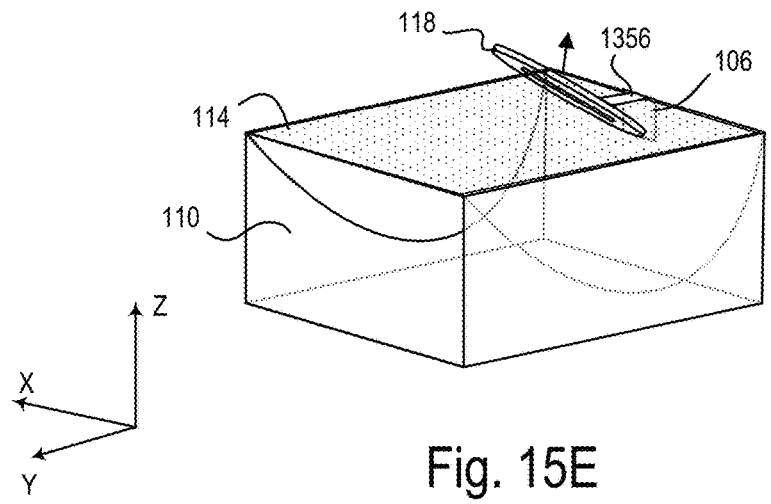
Figure 15F:
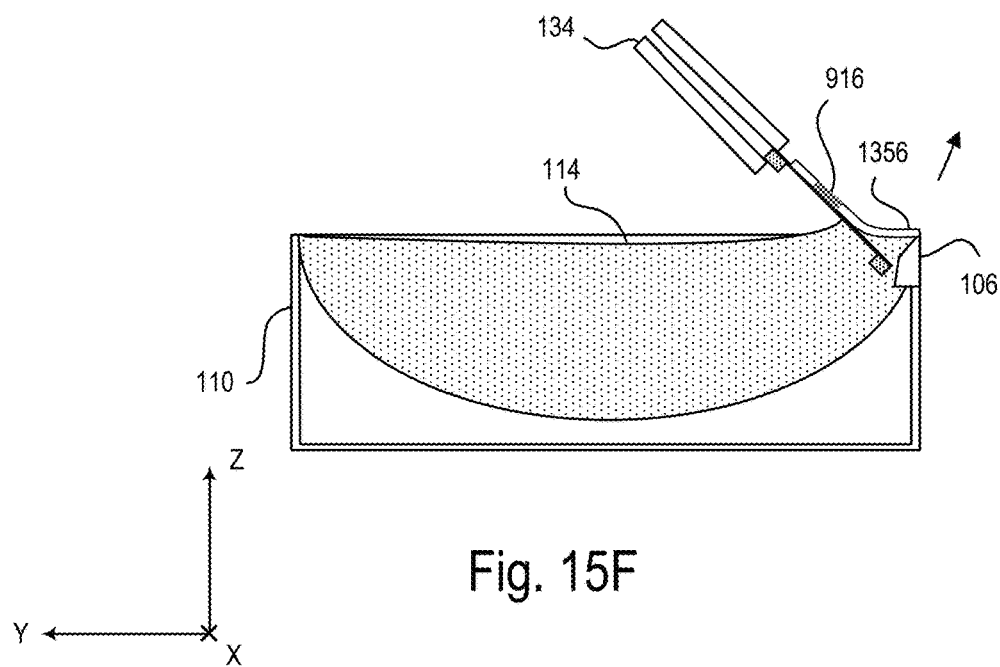

Referring next to FIGS. 14A-14B and 15A-15D, the plate 118 is positioned in the liquid 114, then advanced along the −Y direction toward the blade 106 so as to be positioned under the one or more floating sections 916 while the last section 1356 remains attached to the blade 106 (1215). The plate 118 is inserted into the liquid 114 at an angle, such as, for example, 25-75° relative to the Y direction. As shown in FIGS. 15B and 15D, a meniscus of the liquid 114 rides up the slope of the plate 118 higher than the top edge (the sharp side) of the blade 106 and the undisturbed level at which the liquid rises. The plate 118 is positioned in the liquid 114 and under the one or more floating sections 916 by positioning the plate 118 such that at least one sample 902 of a section 916 is positioned so as to be picked up in the transparent region defined in the opening 122 of the plate 118 in the next motion, which is shown in FIGS. 15E-15F and 16A-16D.

The one or more floating sections 916 are naturally pushed up the slope of the plate 118 as they float on the surface of the liquid 114 and the plate 118 is lifted up from under it, as described next. Referring to FIGS. 15E-15F and 16A-16B, the one or more floating sections 916 are clung to the plate 118 (1220). The one or more floating sections 916 can be clung to the plate 118 by lowering a level of the liquid 114 so that the one or more floating sections 916 are lowered onto the plate 118 (for example, lowering the liquid 114 in the −Z direction). The one or more floating sections 916 can be clung to the plate 118 by lowering the one or more floating sections 916 onto the plate 118 such that the sample 902 of the floating section 916 is positioned over the transparent region defined in the opening 122 of the plate 118. The one or more floating sections 916 can be clung to the plate 118 by first raising the level of the liquid 114 (for example, along the +Z direction) before lowering the level of the liquid 114 (for example, along the −Z direction). As discussed above, the transparent region of the plate 118 can include a plastic film across the opening 124 defined within the plate 118. Thus, at least a portion of each section 916 that includes the sample 902 can be clung to the plastic film. The clinging can happen as the liquid 114 drains from the gap between the sections 916 and the plate 118.

Figure 16A:
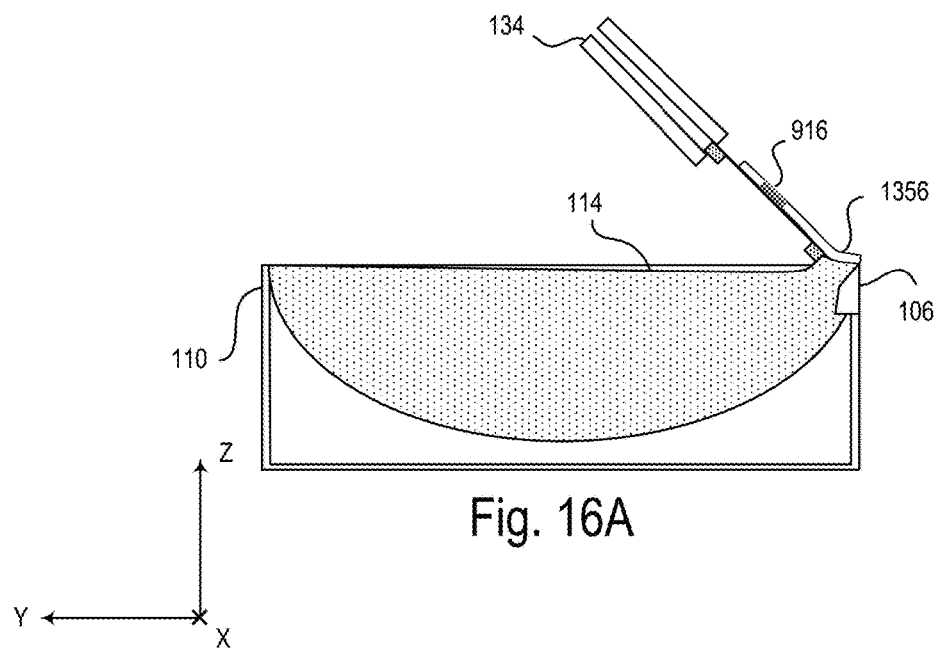
Figure 16B:
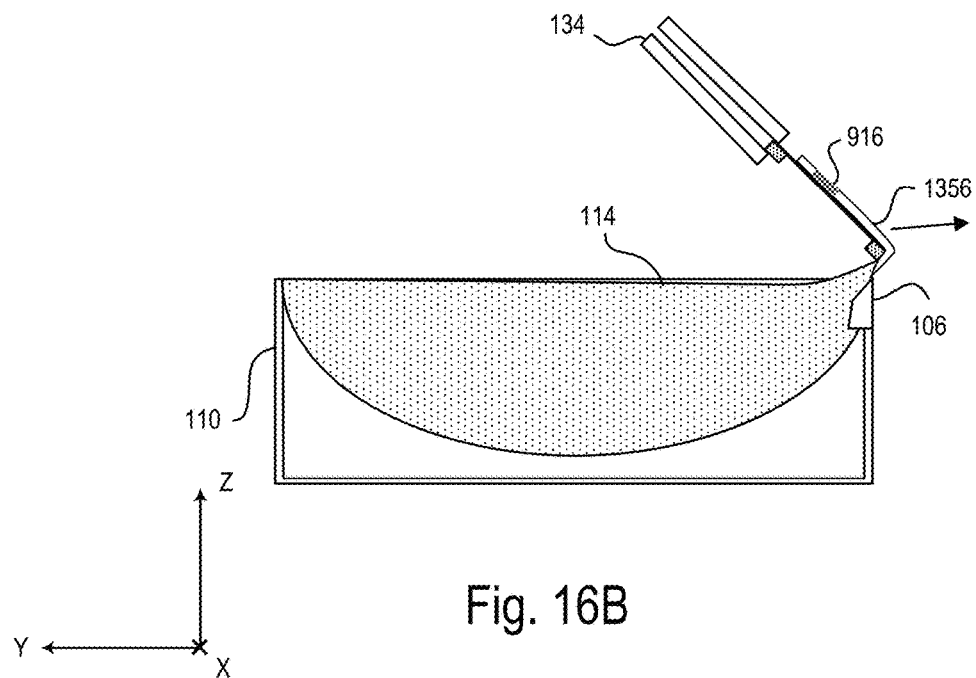
Figure 16C:
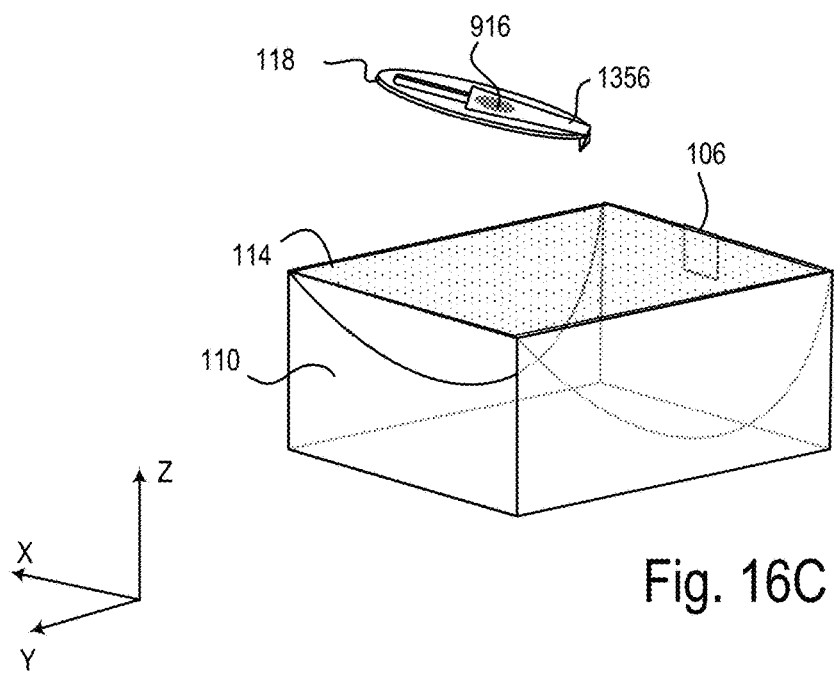
Figure 16D:
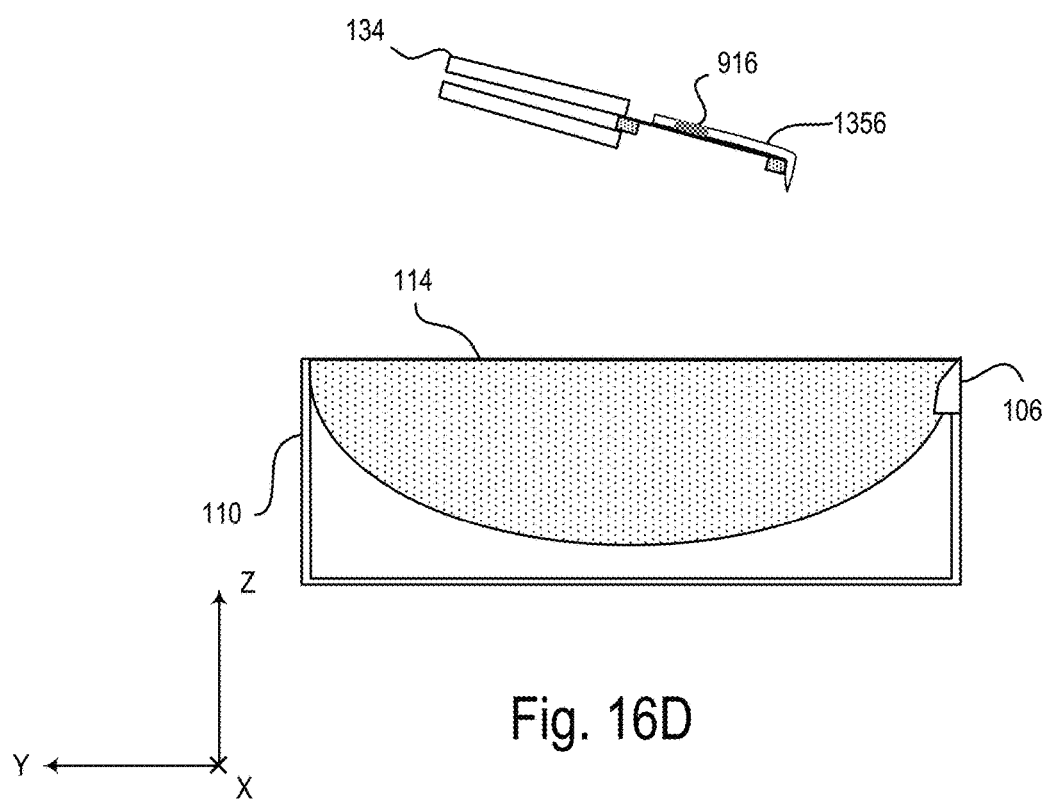

Referring to FIGS. 16A16D, the last section 1356 (which is the only floating section 916) that is attached to the blade 106 is removed from the blade 106 after at least one section 916 is clung to the plate 118 (1225). Once the last section 1356 is removed from the blade 106 (1225) and the sections 916 are clung to the plate 118, the plate 118 is removed from the cavity and the liquid 114 of the trough 110, as shown in FIGS. 16C and 16D.

The procedure 1200 can continue to an optional step of removing liquid 114 which may have clung to the plate 118 from the plate 118 after the plate 118 has been removed from the liquid 114. For example, the liquid 114 can be removed by blotting the liquid 114 such as by touching the plate 118 to an absorbent material.

Figure 13A:
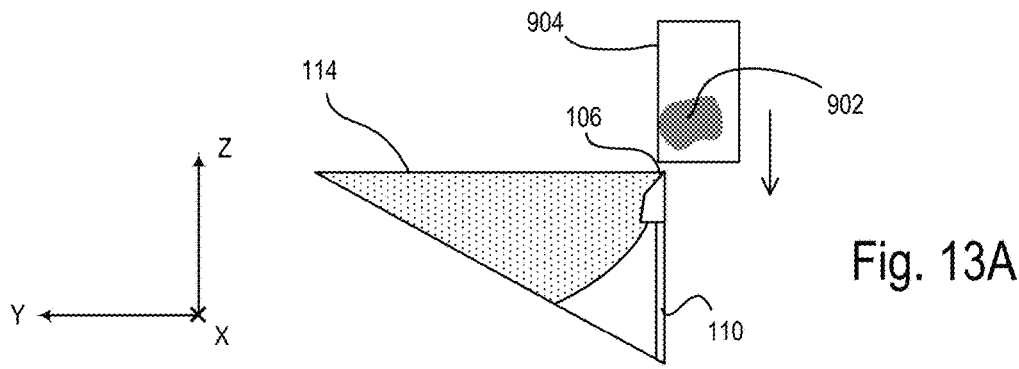
FIGS. 13A-13D are side cross sectional views showing an exemplary progression of a sample block across a blade located next to a liquid of the microtome of FIG. 1.
Figure 13B:
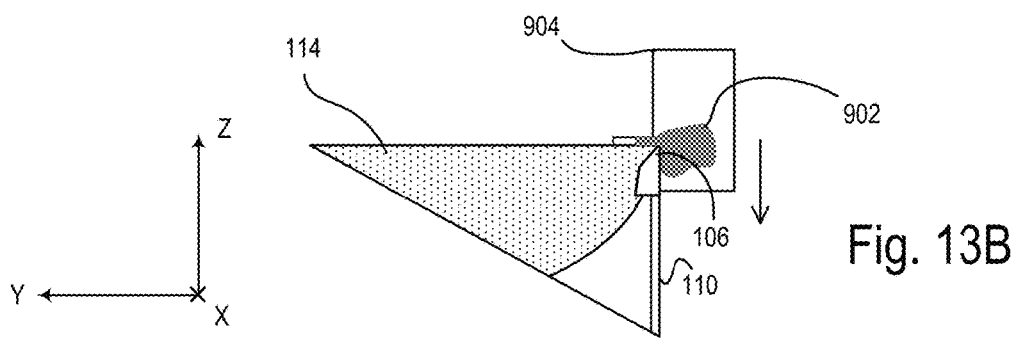
Figure 13C:
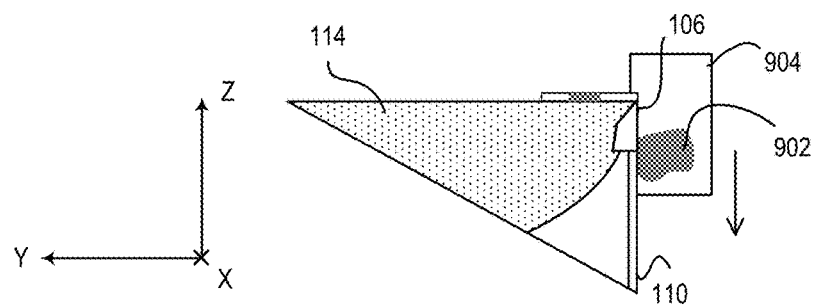
Figure 13D:
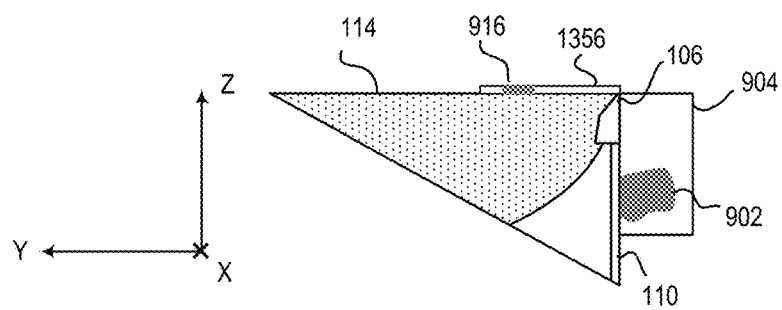
Figure 14A:
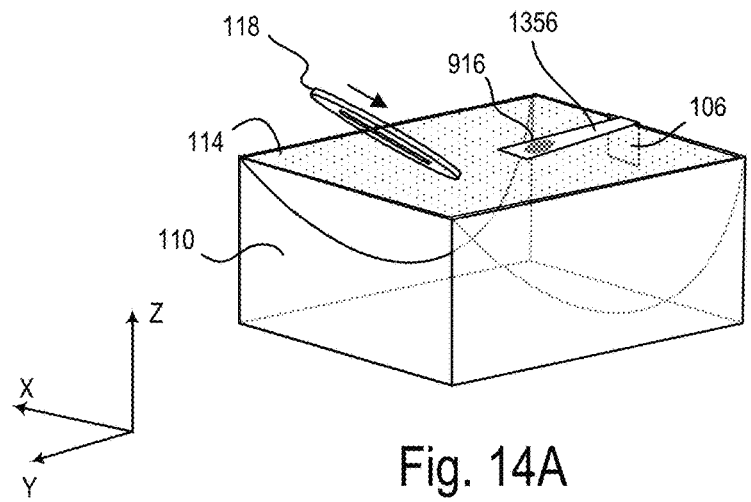
FIGS. 14A, 15A, 15C, 15E, and 16C are exemplary perspective views showing how the section or sections are clung to the plate.
Figure 14B:
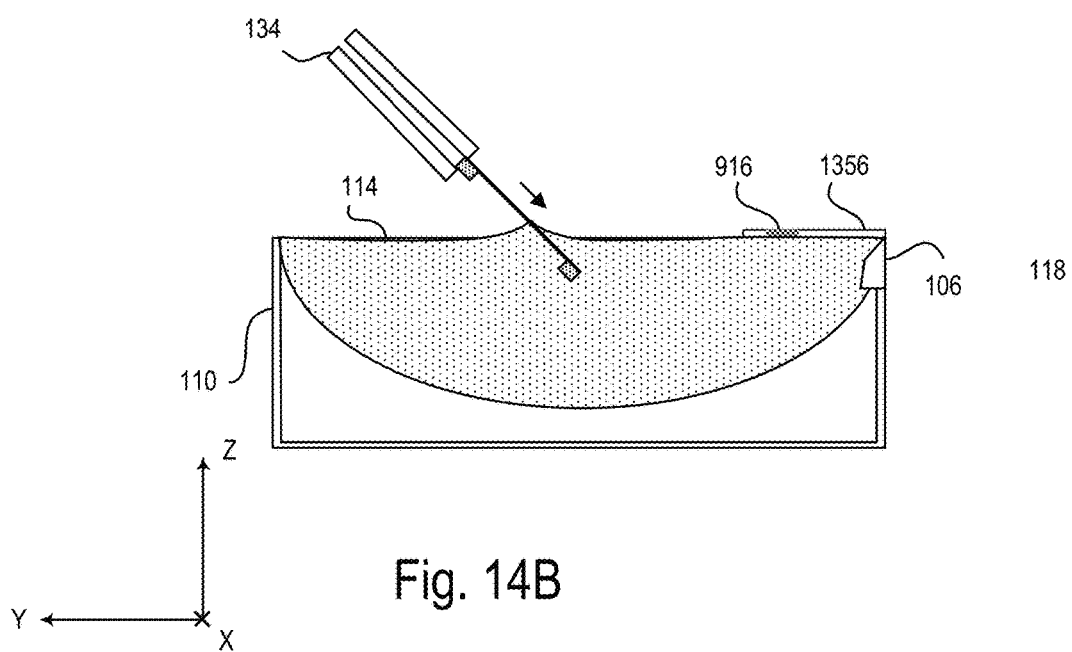
FIGS. 14B, 15B, 15D, 15F, 16A, 16B and 16D are exemplary side cross sectional views showing how the section or sections are clung to the plate.

In the example shown in FIGS. 9, 13A-13D, 14A-14B, 15A-15F, and 16A-16D, the sample block 904 is passed across the blade 106 one time during the procedure 1200 such that one section 916 floats on the liquid 114. The one section 916 that floats on the liquid 114 includes a sample region that includes the at least one sample 902 and the blank region that lacks the at least one sample 902. In this way, the floating section 916 is clung to the plate 118 such that the sample region that includes the sample 902 is positioned over the transparent region 124 of the plate 118 and the blank region is positioned over a non-transparent region (which is the flat support frame 120) of the plate 118. Thus, the section 916 cut from the sample block 904 includes the sample region positioned adjacent to the blank region that lacks the sample. The blank region should be long enough to position the sample region over the transparent region of the plate 118 before the at least one section is clung to the plate 118. In order for this relative positioning of the blank and sample regions on the plate 118 to happen, the sample region should be is closer to the blade 106 than the blank region is just before the sample block 904 contacts the blade 106, which is shown in FIG. 13A.

Figure 17:
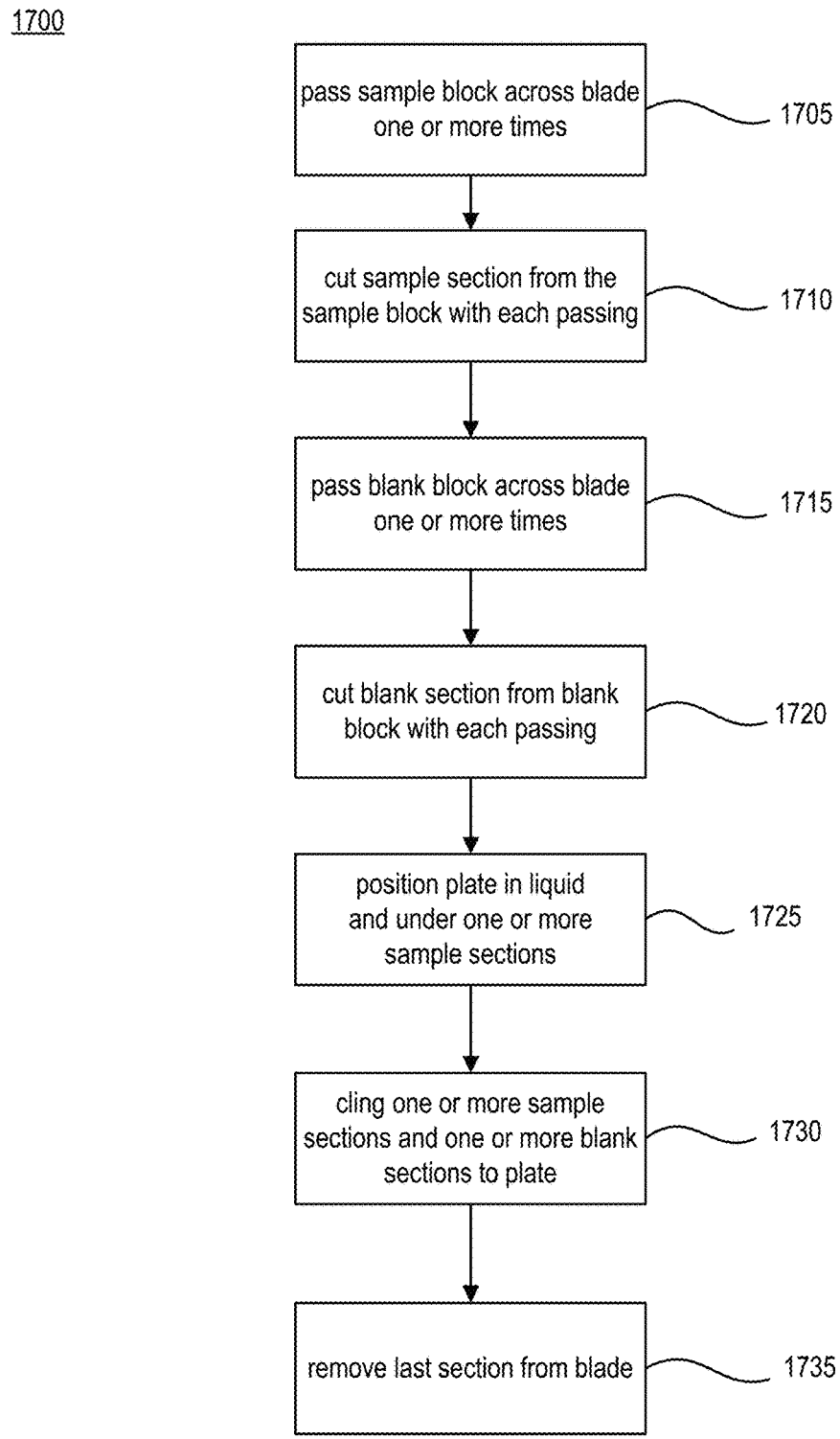
FIG. 17 is a flow chart of an exemplary procedure performed by the microtome of FIG. 1.
Figure 18A:
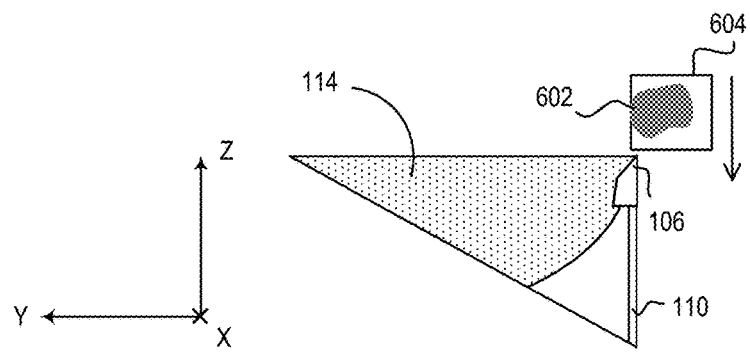
FIGS. 18A-18C are side cross sectional views showing an exemplary progression of a sample block across a blade located next to a liquid of the microtome of FIG. 1 to produce a first cut sample section.
Figure 18B:
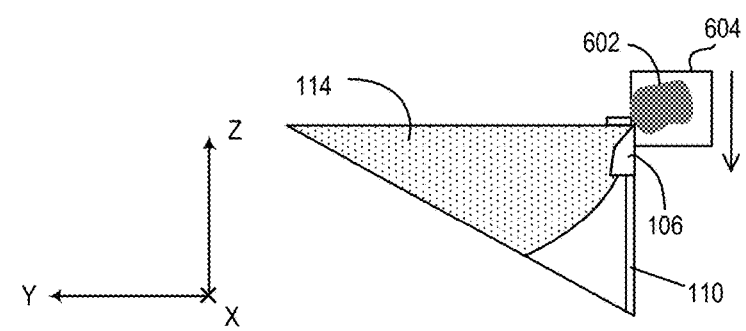
Figure 18C:
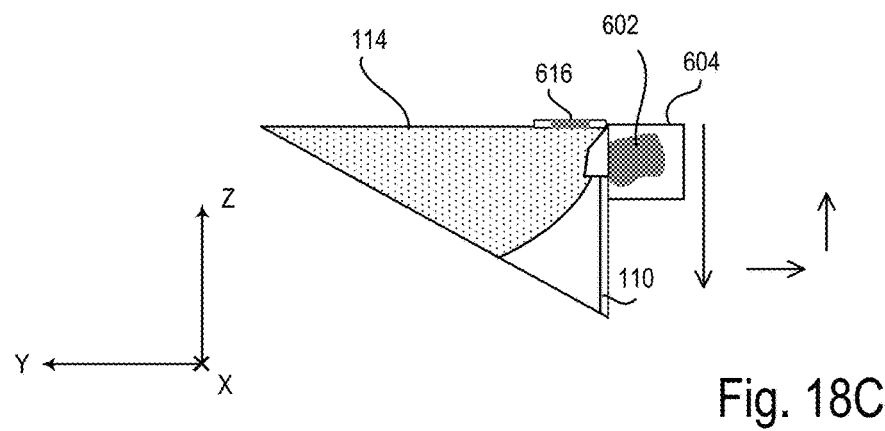
Figure 18D:
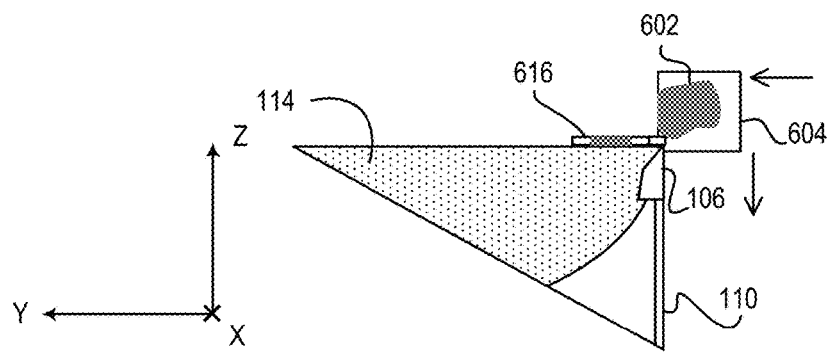
FIGS. 18D-18F are side cross sectional views showing an exemplary progression of a sample block across the blade located next to the liquid of the microtome of FIG. 1 to produce a second cut sample section adjacent the first cut sample section of FIG. 18C.
Figure 18E:
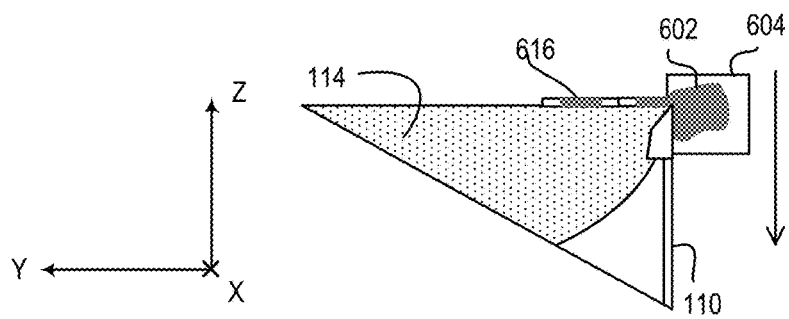
Figure 18F:
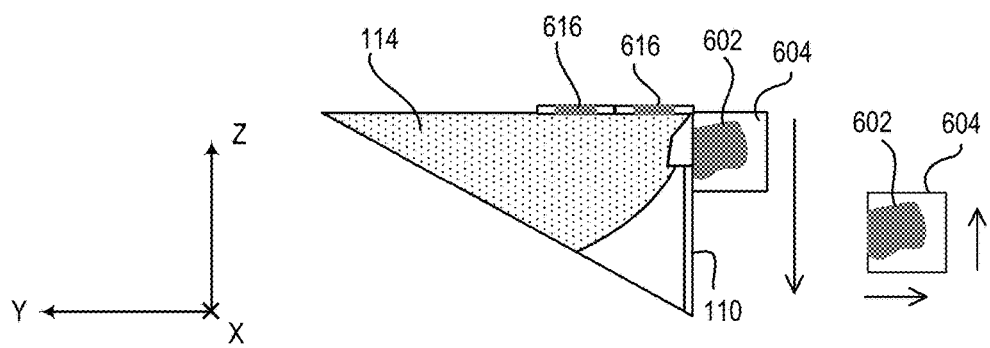

Referring to FIG. 17, a procedure 1700 is performed by the microtome 100 for cutting at least one sample suspended in a sample block of material. The procedure 1700 uses a separate blank block (such as the blank block 638 of FIG. 6 and the blank block 1138 of FIG. 11) to push the sample sections away from the edge of the blade 106 and over the transparent region 124 of the plate 118. The sample block 604 is passed across the blade 106 one or more times (1705). Referring to FIGS. 18A-18C, with each passing of the sample block 604 across the blade 106, a sample section 616 is cut from the sample block 604 (1710). As each sample section 616 is cut, the one or more sample sections 616 float on the liquid 114. In FIG. 18C, the sample section 616 has been cut from the sample block 604 and begins to float on the liquid 114. After the first sample section 616 is cut, if more sample sections 616 are to be cut, then the microtome 100 repositions the sample block 604 above the blade 106 by, for example, translating the sample block 604 along the −Y direction (shown by the arrow in FIG. 18C), translating the sample block 604 along the +Z direction (shown by the arrow in FIG. 18C), and then translating the sample block 604 along the +Y direction (shown by the arrow in FIG. 18D) so that the sample block 604 is ready for the next cut. Referring to FIGS. 18D-18F, the next sample section 616 is then cut from the sample block 604, as shown by the progression in of the sample block 604 along the −Z direction. As the next sample section 616 is cut, it pushes the first sample section 616 further away from the blade 106 and out over the liquid 114.

The number of sample sections 616 that are to be cut can depend on the size of the transparent region that can hold the sample sections 616, the specific sample 602 to be imaged, the size of the sample block 604, or the size of the sample 602, for example. The number of sample sections 616 to be cut can be preset before the sample block 604 is cut, or it can be adjusted during the cutting of the sample block 604. In the example provided next, three sample sections 616 are cut before proceeding to the next steps, which are described with reference to FIGS. 19A-19C.

Figure 19A:
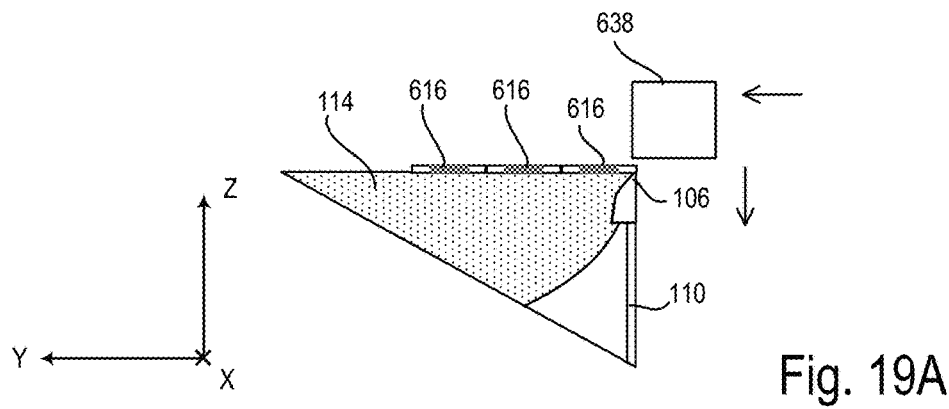
FIGS. 19A-19C are side cross sectional views showing an exemplary progression of a blank block across the blade located next to the liquid of the microtome of FIG. 1 to produce a pusher section adjacent the a third cut sample section.
Figure 19B:
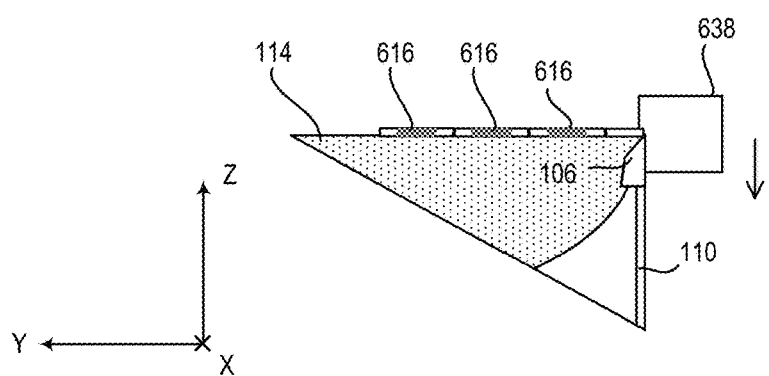
Figure 19C:
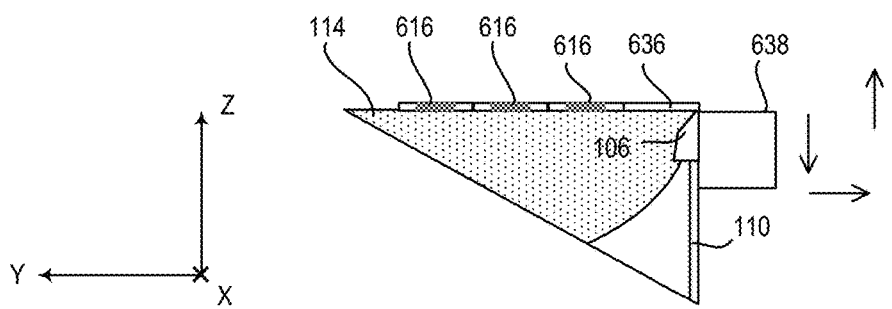

With reference to FIGS. 19A-19C, if all of the sample sections 616 have been cut, then the blank block 638 (which lacks the sample) is passed across the blade 106 one or more times (1715). With each passing of the blank block 638 across the blade 106, a pusher section 636 is cut from the blank block 638 such that one or more pusher sections 636 float on the liquid 114 and a last pusher section remains attached to the blade 106 (1720), as shown in FIG. 19C. For example, in FIG. 6, only one pusher section 636 is cut and this constitutes the last pusher section. As another example, in FIG. 11, two pusher sections 1136 are cut, and the second pusher section 1136 that is cut constitutes the last pusher section (which remains attached to the blade 106, as shown in FIG. 11).

Figure 20A:
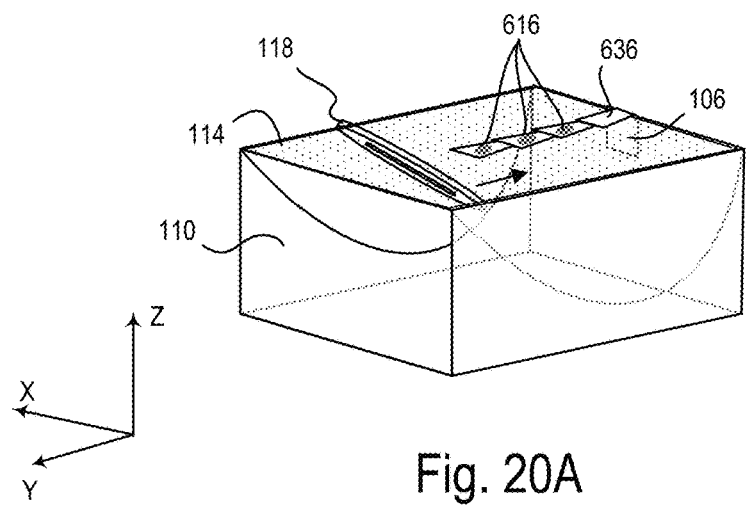
FIGS. 20A, 20C, and 21A are exemplary perspective views showing how the section or sections are clung to the plate.
Figure 20B:
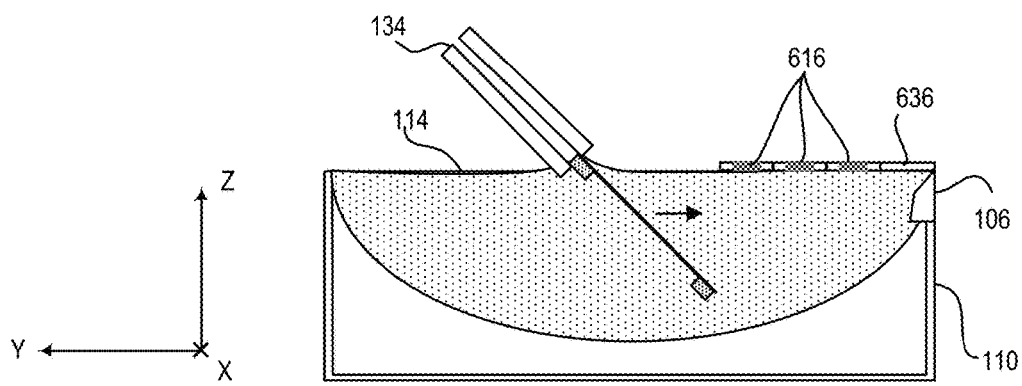
FIGS. 20B, 20D, 20E, 20F, and 21B are exemplary side cross sectional views showing how the section or sections are clung to the plate.
Figure 20C:
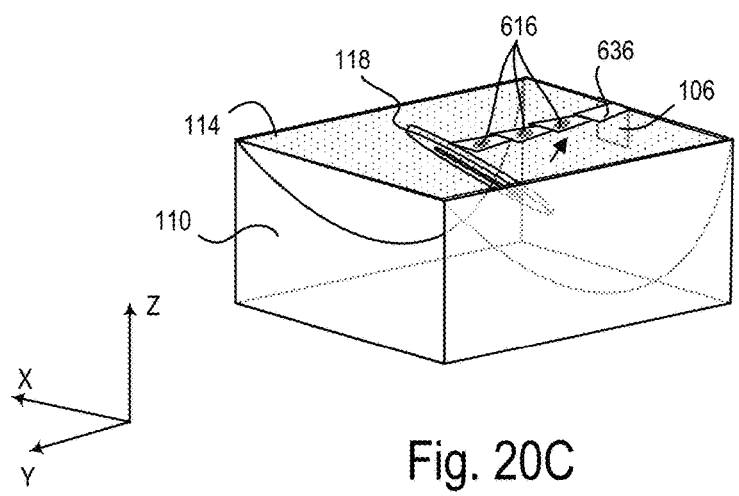
Figure 20D:
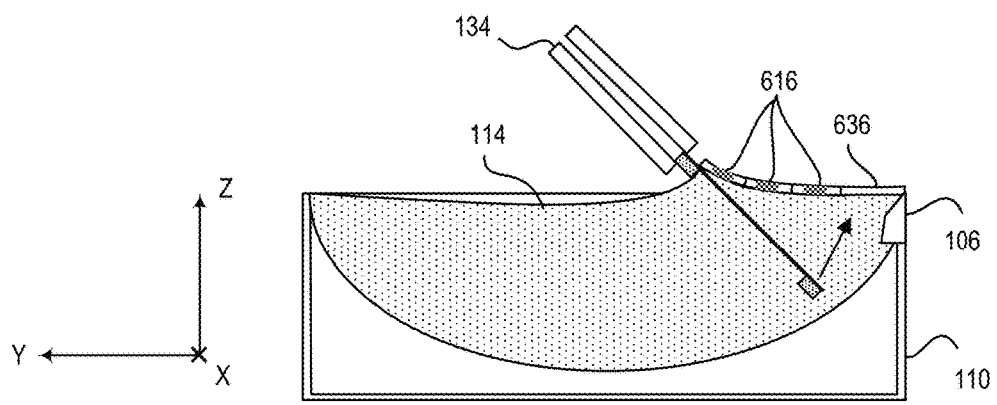
Figure 20E:
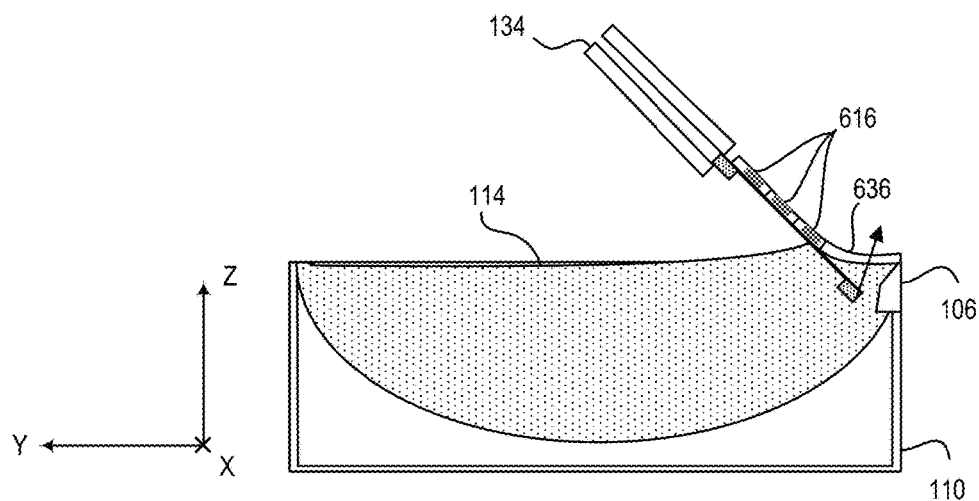
Figure 20F:
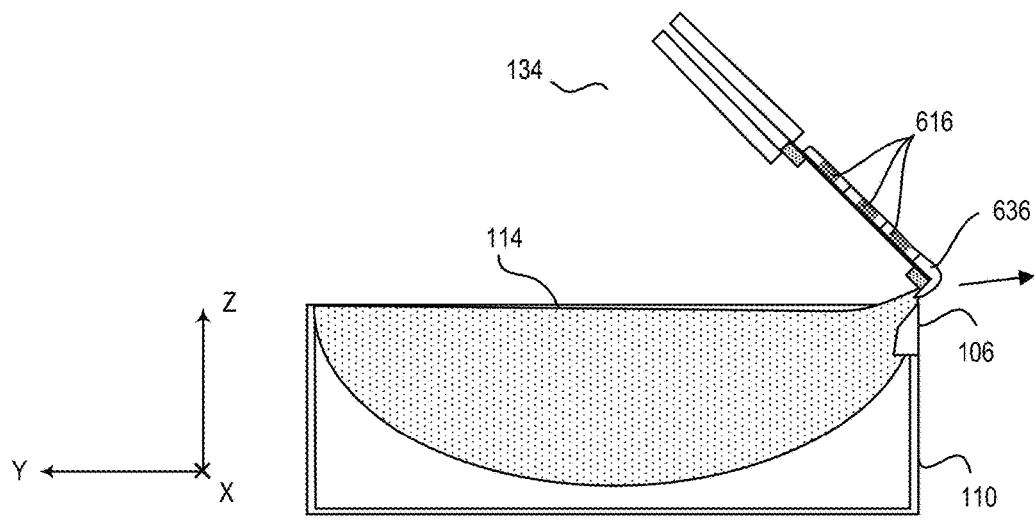

Next, the plate 118 that includes the transparent region 124 is placed in the liquid 114, then advanced along the −Y direction toward the blade 106 so as to be positioned under at least the one or more sample sections 616 (1725). The progression of the plate 118 is shown in FIGS. 20A-20D. The plate 118 is inserted into the liquid 114 at an angle, such as, for example, 25-75° relative to the Y direction. As shown in FIGS. 20B and 20D, a meniscus of the liquid 114 rides up the slope of the plate 118 higher than the top edge (the sharp side) of the blade 106 and the undisturbed level at which the liquid rises.

The one or more sample sections 616 and the one or more pusher sections 636 are clung to the plate 118 (1730). An exemplary progression of the one or more sample sections 616 and the one or more pusher sections 636 being clung to the plate 118 is shown in FIGS. 20C-20F.

The one or more sample sections 616 are naturally pushed up the slope of the plate 118 as they float on the surface of the liquid 114 and the plate 118 is lifted up from under it. Once at least one of the sample sections 616 is clung to the plate, then the last pusher section is removed from the blade 106 (1735), as shown by the progression from FIG. 20F to FIG. 21B (which is viewed in a perspective in FIG. 21A). The plate 118 can be positioned in the liquid 114 and under the one or more sample sections 616 by positioning the plate 118 such that at least one of the samples 602 of a sample section 616 is positioned across the transparent region over the opening 122 of the plate 118. The plate 118 is positioned in the liquid 114 and under at least the one or more sample sections 616 (1725) while the last pusher section remains attached to the blade 106.

Figure 21A:
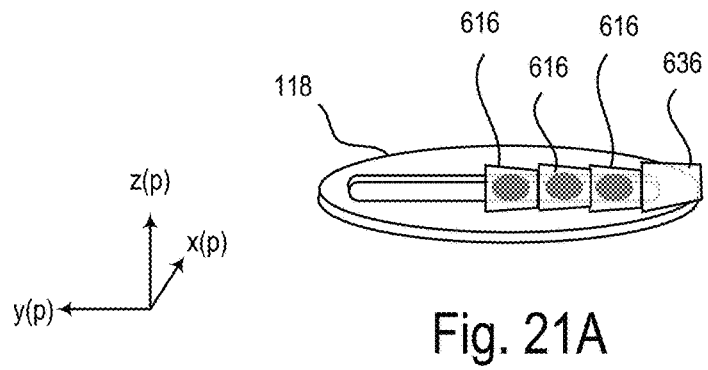
Figure 21B:
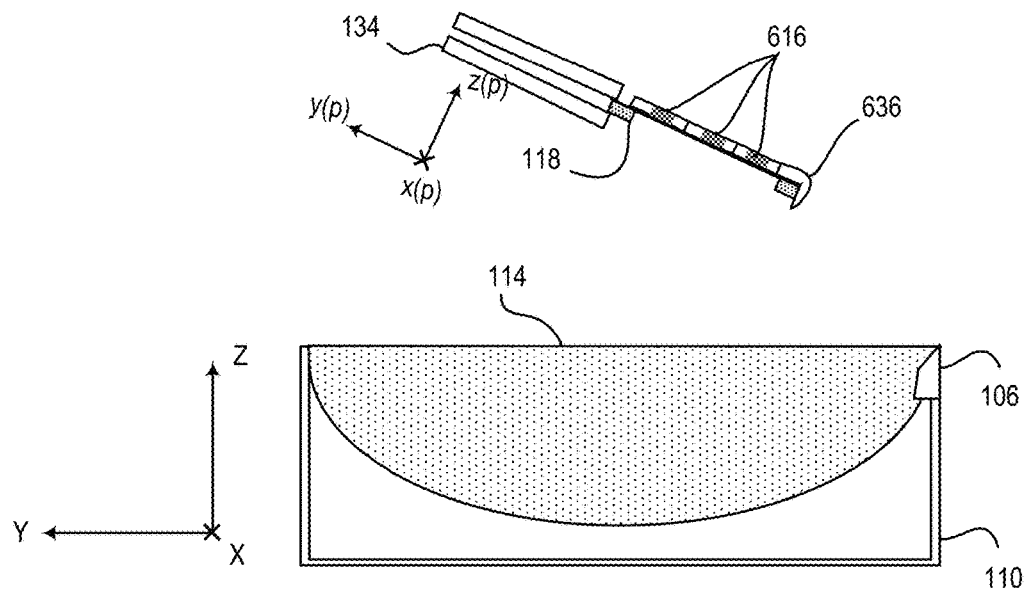

Additionally, after the last pusher section is removed from the blade 106 (1735), the plate 118 (on which the sample sections 616 are clung) is removed from the cavity 112 and the liquid 114, as shown in FIGS. 21A and 21B.

The one or more sample sections 616 and the one or more pusher sections 636 can be clung to the plate 118 by lowering a level of the liquid 114 relative to the plate 118 so that all of the sample sections 616 (and the one or more pusher sections 636) are lowered with the liquid 114 onto the plate 118. The one or more sample sections 616 can be clung to the plate 118 by lowering the sample sections 616 onto the plate 118 such that the samples 602 of the sample sections 616 are positioned over the transparent region over the opening 122 of the plate 118. In some implementations, the one or more sample sections 616 and the one or more pusher sections 636 can be clung to the plate 118 by raising the level of the liquid 114 before lowering the level of the liquid 114.

With each passing of the sample block 604 across the blade 106 after the first pass of the sample block 604, after the sample section 616 is cut from the sample block 604, the sample section 616 sticks to the last sample section 616 that was cut and is floating in the liquid 114.

The one or more sample sections 616 and the one or more pusher sections 636 can be clung to the plate 118 by clinging at least a portion of each sample section 616 to the plastic film and clinging at least a portion of the one or more pusher sections to the non-transparent region (the flat support frame 120).

Figure 22:
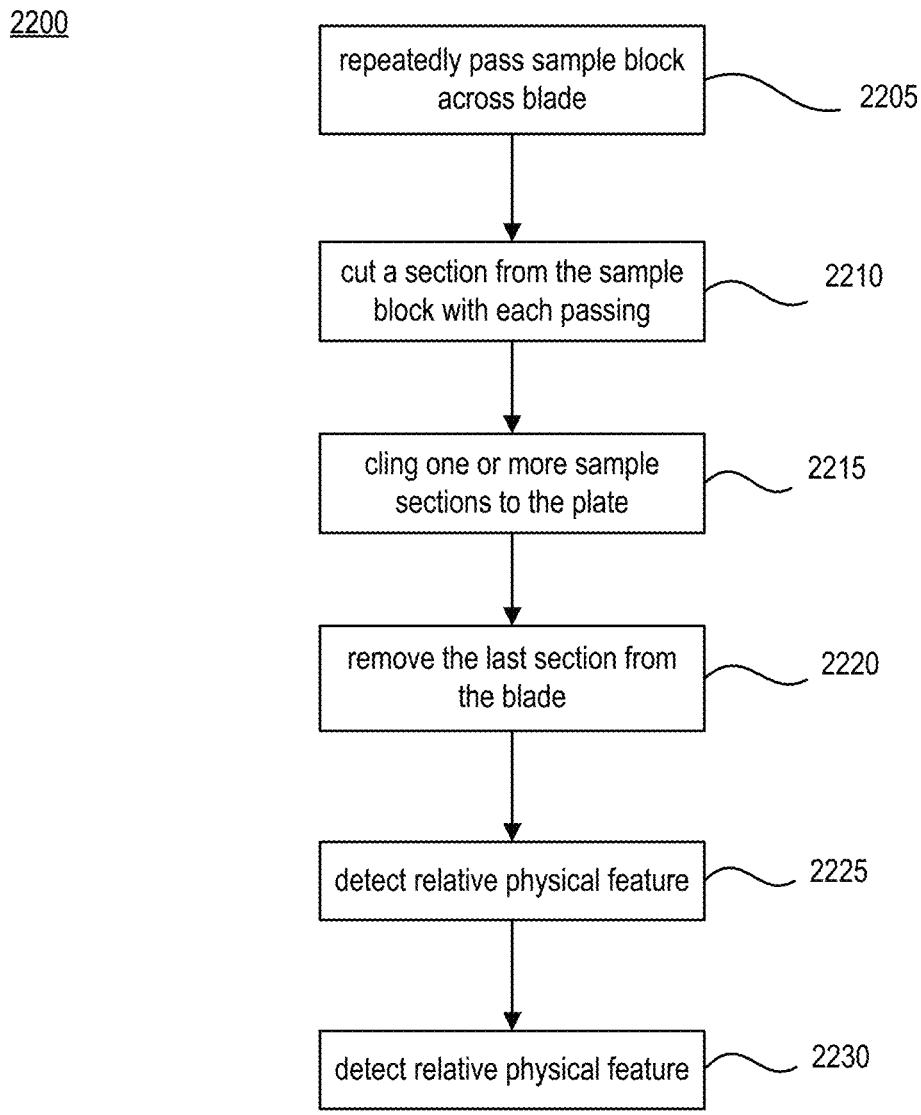
FIG. 22 is a flow chart of an exemplary procedure performed by the microtome of FIG. 1.

Referring to FIG. 22, a procedure 2200 is performed by the microtome 100 for cutting a sample 102 suspended in a sample block 104 of material. The procedure 2200 is carried out under control of the control system 148. The sample block 104 is repeatedly passed across the blade 106 (2205), and with each passing of the sample block 104 across the blade 106, a sample section 116 is cut from the sample block 104 (2210). A plurality of sample sections 116 float on the liquid 114 remain adhered to each other. And, at least one of the sample sections 116 or a pusher section (such as section 136) remains attached to the blade 106. The plurality of sample sections 116 are clung to the plate 118 (2215), and the at least one sample section or the pusher section that remains attached to the blade 106 is removed from the blade (2220).

The control system 148 receives a measurement of a detected relative physical feature between one or more of the blade, the trough, the liquid, the plate, and the sample block (2225) from the measurement system 146. The relative physical feature that can be detected can be a distance between the blade 106 and the sample block 104 before the sample block 104 is passed across the blade 106. The relative physical feature that can be detected can be an angle between the blade 106 and the sample block 104 before the sample block 104 is passed across the blade 106. The relative physical feature can be a distance between the plate 118 and the blade 106. The relative physical feature can be an electrical feature between the plate 118 and the liquid 114.

The control system 148 performs a data analysis on the measurement or measurements, and based on the analysis, controls one or more of the passing, the cutting, the clinging, and the removing based on the detected relative physical feature (2230). The control is carried out by sending one or more signals to the actuation systems 140, 142, 144 coupled to the respective components of the microtome 100.

In particular, the distance between each sample section 116 and the blade 106 can be measured, then stored within the control system 148, and recalled to establish the correct cutting position of the blade 106. This repositioning is done to a few nanometer accuracy after the blade to section distance has been changing while doing other motions, such as, for example, cutting a different section from the sample block or cutting a pusher section from the blank block. The repositioning to nanometer accuracy is also key to being able to cut the sample section and a separate pusher section both with nanometer control of the thickness of the sections.

Figure 23:
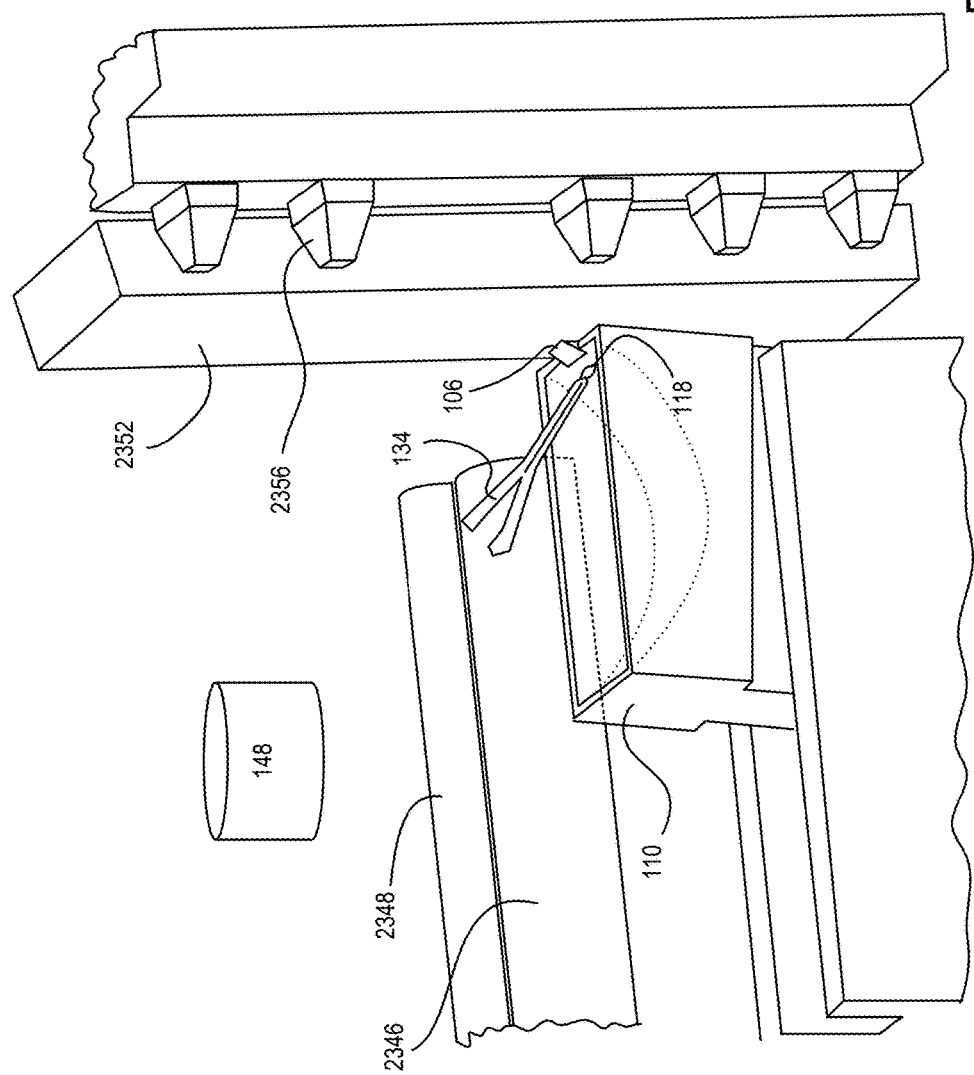
FIG. 23 is a perspective view of an exemplary measurement system of the microtome of FIG. 1.
Figure 24:
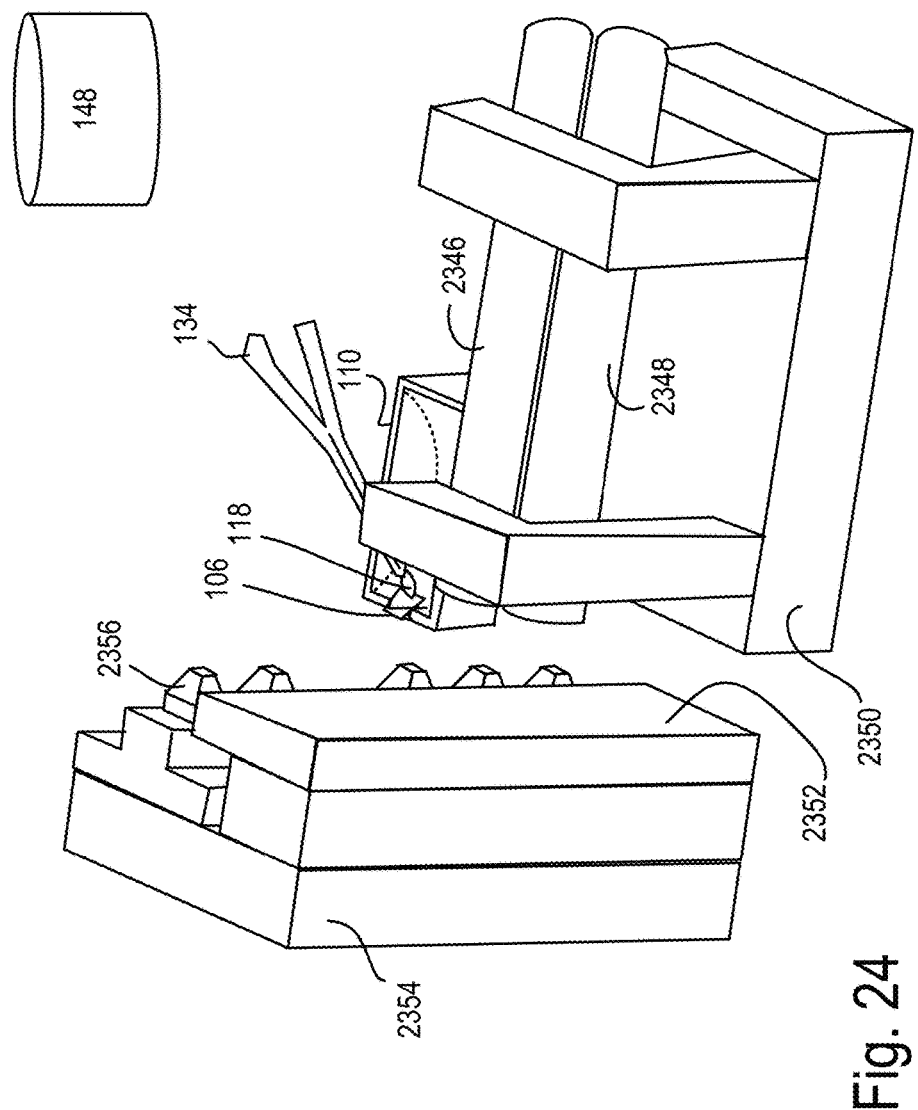
FIG. 24 is another perspective view of the exemplary measurement system of FIG. 22.
Figure 25:
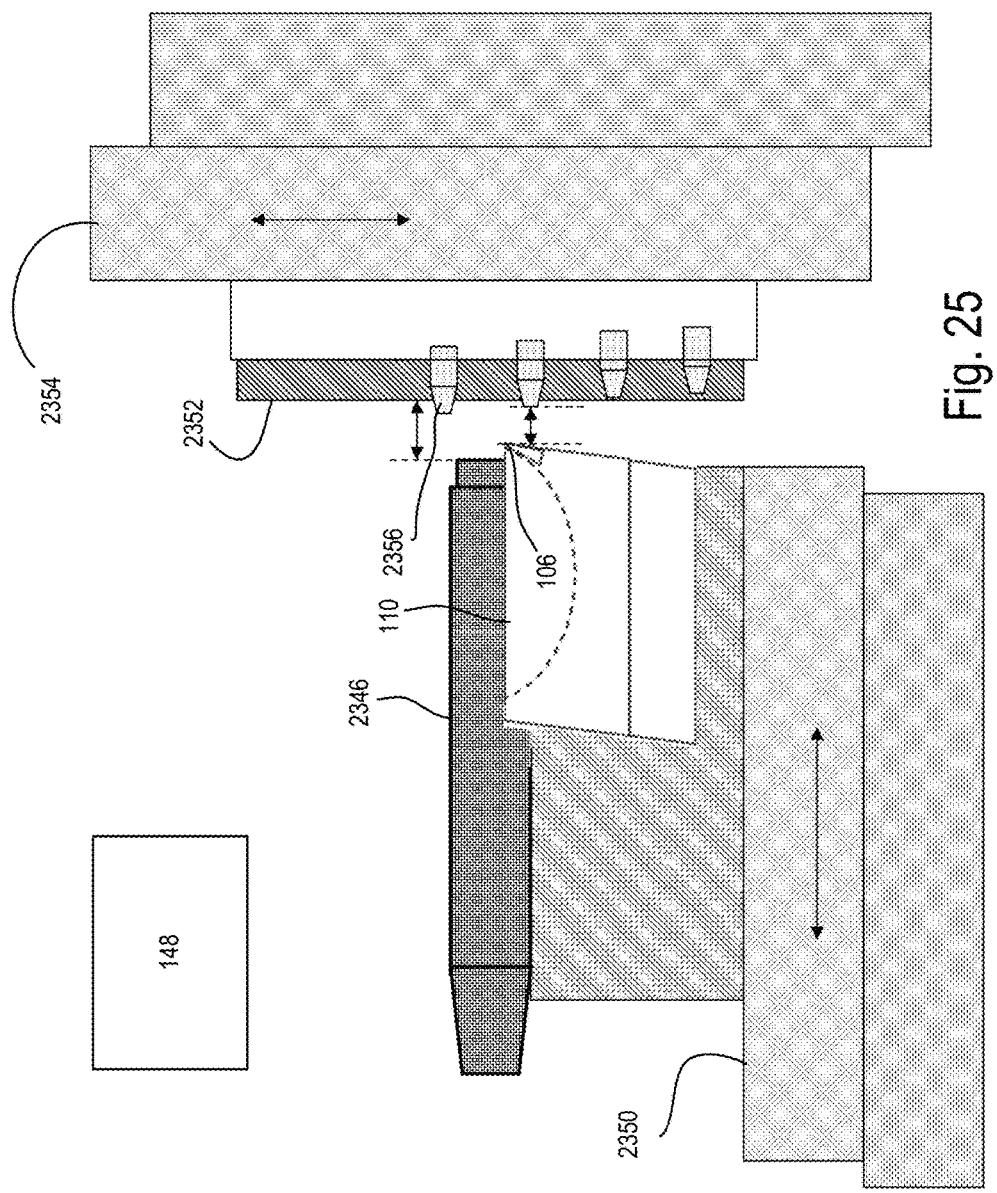
FIG. 25 is a side cross sectional view of the exemplary measurement system of FIGS. 23 and 24.

Referring to FIGS. 23-25, in some implementations, the measurement system 146 includes a multi-phase interferometer 2346 attached to the mount or assembly 2350 (shown in FIG. 24) that also holds the trough 110 and the blade 106, and a reflective optic 2352 (such as a mirror) fixedly attached (directly or indirectly) to the mount or assembly 2354 (shown in FIG. 24) that also holds the sample block and/or the blank block. Each sample block or blank block is mounted on a respective block mount 2356. Since both assemblies 2350 and 2354 are rigid assemblies, the distance between the interferometer 2346 and the mirror 2352 is directly related to the distance between the sample block and/or the blank block and the blade 106. Additionally, if there is any possibility of rotation of one assembly (such as the block assembly) to the other assembly (such as the blade assembly), then a second interferometer 2348 can be placed next to the first interferometer. And, the second interferometer 2348 can be configured to measure a rotation between or an angle between the two assemblies 2350, 2354. In this way, both translation and rotation of the two assemblies 2350, 2354 can be used to properly position the blade 106 with respect to the sample block or the blank block.

The microtome 100 described herein enables an operator to section larger volumes over longer periods of time with less human effort would allow the complete sectioning of larger and more complex organisms. Additionally, the microtome 100 described herein can produce thin, minimally deformed sections in which the samples are also less deformed than the previous non-automated systems, which allows for increased observation of tissue samples.

In the microtome 100, the plate 118 is held within the grasper 134, and the microtome 100 determines a spatial relationship between the plate 118 and the blade 106. The one or more sample sections and the one or more pusher sections can be cut for just one plate 118. Then, the cut sections (the one or more sample sections and any pusher sections if they are present or the blank region) are clung to the plate and dried, and the plate 118 is stowed, and the process can start all over again. Thus, the interval between cutting each section remains the same throughout the procedure and can be consistently reproduced with each step. If a plurality of sample sections are cut for each plate 118 (for example, three sample sections and one pusher section such as shown in FIGS. 20A-20F), the sample sections can be cut at intervals of 10 seconds to about 1 minute (where the interval is the time between completion of each sample section cut). The overall procedure (from the first cut to the placement of the plate 118 in the storage) can take between about 6-15 minutes. Because the time intervals are long compared with the drift effects within the microtome 100, the interferometer can be used to help counteract the influence of drift within the microtome 100.

Figure 26:
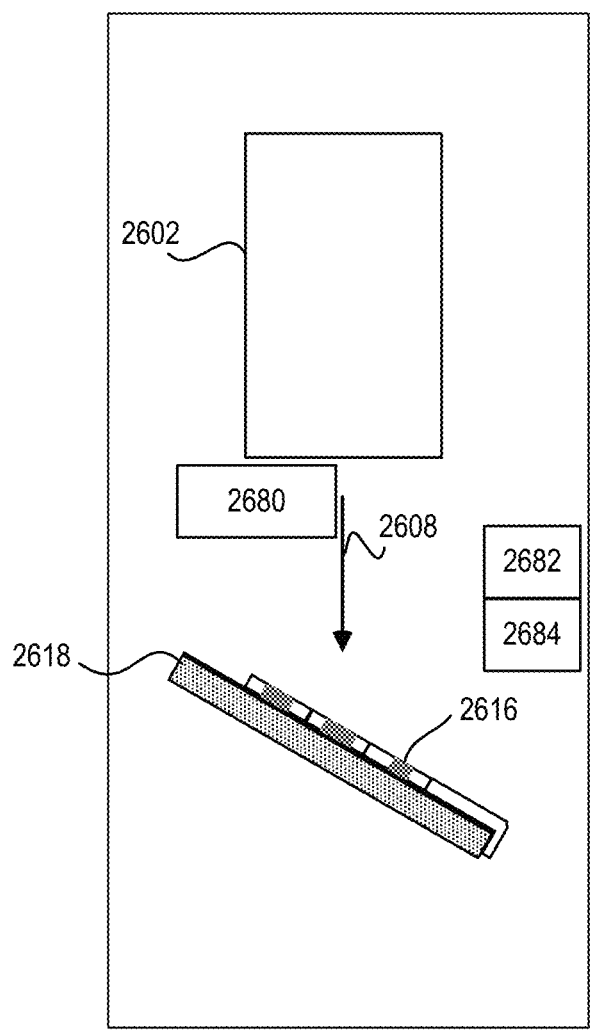
FIG. 26 is a block diagram of an exemplary SEM that receives the plate with the cut sections.

Referring also to FIG. 26, in other implementations, another kind of plate 2618 can be designed without an opening 122 so that it can be used in a scanning electron microscope (SEM) 2600, which produces images of the sample section 2616 on the plate 2618 by scanning the plate 2618 and the sample with a focused beam of electrons 2608 produced by an electron source system 2602. The electrons in the beam 2608 interact with atoms in the sample, producing various signals that can be detected and that contain information about the sample's surface topography and composition. The electron beam 2608 is generally scanned in a raster scan pattern, and the beam's position is combined with the detected signal to produce an image. A SEM can achieve a resolution of better than 1 nanometer. The biological samples can be observed in high vacuum, in low vacuum, in wet conditions (in environmental SEM), or at a wide range of cryogenic or elevated temperatures. The most common mode of detection in an SEM is by secondary electrons emitted by atoms within the sample that are excited by the electron beam 2608. On a flat surface, the plume of secondary electrons is mostly contained by the sample, but on a tilted surface, the plume is partially exposed and more electrons are emitted. By scanning the sample and detecting the secondary electrons, an image displaying the topography of the surface is created.

The energy exchange between the electron beam 2608 and the sample on the section of the plate 2618 results in the reflection of high-energy electrons by elastic scattering, emission of secondary electrons by inelastic scattering, and the emission of electromagnetic radiation, each of which can be detected by specialized detectors 2680, 2682, 2884 placed relative to the plate 2618 (and the sample sections 2616) for viewing. The beam current absorbed by the sample can also be detected and used to create images of the distribution of current throughout the sample.

In some implementations, the plate 2618 could be made of glass to enable a correlative microscopy in which it is first used in a light microscopy environment and then used in an SEM.

Other implementations are within the scope of the following claims.

What is claimed is:

1. A method of cutting at least one sample suspended in a sample block of material, the method comprising:
passing the sample block across a blade one or more times;
with each passing of the sample block across the blade, cutting a sample section from the sample block, wherein one or more sample sections float on a liquid;
passing a blank block across the blade one or more times, wherein the blank block lacks the sample;
with each passing of the blank block across the blade, cutting a pusher section from the blank block, wherein one or more pusher sections float on the liquid and a last pusher section remains attached to the blade;
positioning a plate that includes an imaging region in the liquid and under at least the one or more sample sections;
clinging the one or more sample sections and the one or more pusher sections to the plate; and
removing the last pusher section from the blade.

2. The method of claim 1, further comprising removing the plate from the liquid after the one or more sample sections and the one or more pusher sections are clung to the plate.

3. The method of claim 1, wherein positioning the plate in the liquid and under the one or more sample sections comprises positioning the plate such that at least one of the samples of a sample section is positioned across the imaging region of the plate.

4. The method of claim 1, wherein clinging the one or more sample sections and the one or more pusher sections to the plate comprises removing the liquid between the one or more sample sections and the one or more pusher sections and the plate.

5. The method of claim 1, wherein clinging the one or more sample sections and the one or more pusher sections to the plate comprises lowering a level of the liquid relative to the plate so that all of the sections are lowered with the liquid onto the plate.

6. The method of claim 5, wherein clinging the one or more sample sections to the plate comprises lowering the sample sections onto the plate such that the samples of the sample sections are positioned over the imaging region of the plate.

7. The method of claim 5, wherein clinging the one or more sample sections and the one or more pusher sections to the plate comprises raising the level of the liquid before lowering the level of the liquid.

8. The method of claim 1, wherein, with each passing of the sample block across the blade after the first pass of the sample block, after the sample section is cut from the sample block, the sample section sticks to the last sample section that was cut and is floating in the liquid.

9. The method of claim 1, wherein the plate is positioned inside the liquid and under at least the one or more sample sections while the last pusher section remains attached to the blade.

10. The method of claim 9, wherein removing the last pusher section from the blade comprises removing the last pusher section from the blade after at least one of the sample sections is clung to the plate.

11. The method of claim 1, wherein the imaging region is a transparent region, the plate comprises a non-transparent region that provides a frame and defines the transparent region, and the transparent region includes a plastic film that extends across the transparent region and is secured to the non-transparent region.

12. The method of claim 11, wherein clinging the one or more sample sections and the one or more pusher sections to the plate comprises clinging at least a portion of each sample section to the plate so that the sample in each sample section is adjacent the transparent region, and clinging at least a portion of the one or more pusher sections to the plate so that the pusher sections extend across the non-transparent region.

13. The method of claim 1, wherein passing the sample block across the blade comprises passing the sample block across the blade one time such that one sample section floats on the liquid.

14. The method of claim 1, wherein passing the blank block across the blade comprises passing the blank block across the blade one time such that one pusher section floats on the liquid.

15. The method of claim 1, wherein passing the sample block across the blade comprises passing the sample block across the blade a plurality of times such that a plurality of sample sections float on the liquid.

16. The method of claim 1, wherein passing the blank block across the blade comprises passing the blank block across the blade a plurality of times such that a plurality of pusher sections float on the liquid.

17. The method of claim 1, wherein positioning the plate in the liquid and under the one or more floating sections comprises moving one or more sections and the plate with respect to each other such that the sections ride up a meniscus of the liquid that initially separates sections from the plate.

18. The method of claim 1, wherein each sample section has a thickness of 20 nanometers to 2 micrometers.

19. A method of cutting a sample suspended in a sample block of material, the method comprising:
  repeatedly passing a sample block across a blade located at the end of a trough that defines a cavity that holds a liquid;
  with each passing of the sample block across the blade, cutting a sample section from the sample block, wherein a plurality of sample sections float onto the liquid held within the trough and remain adhered to each other;
  passing a blank block across the blade one or more times, wherein the blank block lacks the sample, and with each passing of the blank block across the blade, cutting a pusher section from the blank block, at least one pusher section remaining attached to the blade;
  clinging all of the plurality of sample sections to a plate that includes a support frame and an electron-transparent imaging region inside the support frame such that at least a sample in a sample section is positioned over the electron-transparent imaging region;
  removing the pusher section that is attached to the blade from the blade;
  detecting a relative physical feature between one or more of the blade, the trough, the liquid, the plate, and the sample block; and
  controlling one or more of the passing, the cutting, the clinging, and the removing based on the detected relative physical feature.

20. The method of claim 19, wherein detecting the relative physical feature between one or more of the blade, the trough, the liquid, the plate, and the sample block comprises one or more of:
  detecting a distance between the blade and the sample block before the sample block is passed across the blade;
  detecting an angle between the blade and the sample block before the sample block is passed across the blade;
  detecting a distance between the plate and the blade; and
  detecting an electrical feature between the plate and the liquid.

21. The method of claim 19, wherein the pusher section is long enough to position the sample section over the electron-transparent imaging region of the plate.

22. The method of claim 19, further comprising positioning the plate that includes the imaging region in the liquid and under the one or more floating sample sections while the pusher section remains attached to the blade.

23. The method of claim 19, wherein removing the pusher section from the blade comprises removing the pusher section from the blade after at least one of the sample sections is clung to the plate.

24. The method of claim 19, wherein clinging the sample sections to the plate comprises removing the liquid between the sample sections and the plate.

25. The method of claim 19, wherein clinging the sample sections to the plate comprises lowering the sample sections onto the plate such that the sample of the sample section is positioned over the imaging region of the plate.

* * * * *